US008628974B2

(12) United States Patent
Chen et al.

(10) Patent No.: US 8,628,974 B2
(45) Date of Patent: Jan. 14, 2014

(54) PROTEIN/PEPTIDE SEQUENCING BY CHEMICAL DEGRADATION IN THE GAS PHASE

(75) Inventors: Xiaoyu Chen, Westlake Village, CA (US); Michael S. Westphall, Fitchburg, WI (US); Lloyd M. Smith, Madison, WI (US); Brian L. Frey, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 993 days.

(21) Appl. No.: 11/568,536

(22) PCT Filed: Jul. 15, 2005

(86) PCT No.: PCT/US2005/025185
§ 371 (c)(1),
(2), (4) Date: Oct. 31, 2006

(87) PCT Pub. No.: WO2007/015690
PCT Pub. Date: Feb. 8, 2007

(65) Prior Publication Data
US 2008/0248585 A1    Oct. 9, 2008

Related U.S. Application Data

(60) Provisional application No. 60/588,447, filed on Jul. 16, 2004.

(51) Int. Cl.
*G01N 33/00* (2006.01)
*H01J 49/36* (2006.01)
(52) U.S. Cl.
USPC .............. 436/89; 436/800; 422/68.1; 422/73; 422/93; 422/154; 422/158; 250/282

(58) Field of Classification Search
USPC ........ 436/800, 89; 250/282; 422/68.1, 73, 93, 422/99, 100, 104, 158
See application file for complete search history.

(56) References Cited

PUBLICATIONS

Abersold, R., et al., "Design, synthesis and characterization of a protein sequencing reagent yielding amino acid derivatives with enhanced detectability by mass spectrometry," Protein Science, Cambridge University Press, vol. 1, pp. 494-503, 1992.
Walk Tilmann, B., et al., "Identification of unusual amino acids in peptides using automated sequential Edman degradation coupled to direct detection by electrospray-ionization mass spectrometry," Biopolymers, vol. 49, No. 4, pp. 329-340, 1999.
Reid, G., et al., "N-terminal derivatization and fragmentation of neutral peptides via ion-molecule reactions with acylium ions: toward gas-phase Edmand degradation?" J. Amer. Chem. Soc.,vol. 123, No. 6, pp. 1184-1192, 2001.
Reid, G., et al., "Gas-phase concentration, purification, and identification of whole proteins from complex mixtures," J. Amer. Chem. Soc., vol. 124, No. 25, pp. 7353-7362, 2002.

*Primary Examiner* — Krishnan S Menon
*Assistant Examiner* — Rebecca M Fritchman
(74) *Attorney, Agent, or Firm* — Joseph T. Leone, Esq.; DeWitt Ross & Stevens S.C.

(57) ABSTRACT

A fast and sensitive method and device for protein sequencing are disclosed. The method uses a combination of Edman degradation chemistry and mass spectrometry to sequence proteins and polypeptides. A peptide degradation reaction is performed on a polypeptide or protein ion reactant in the gas phase. The reaction yields a first ion product corresponding to a first amino acid residue of the polypeptide or protein reactant and a polypeptide or protein fragment ion. The mass-to-charge ratio for the first ion product, or the polypeptide or protein fragment ion, or both, is then determined. The first amino acid residue of the polypeptide or protein reactant is then identified from the mass-to-charge ratio so determined.

20 Claims, 19 Drawing Sheets

SEQUENCE LISTING

<160> NUMBER OF SEQ ID NOS: 3

<210> SEQ ID NO 1
<211> LENGTH: 7
<212> TYPE: PRT
<213> ORGANISM: Artificial
<220> FEATURE:
<223> OTHER INFORMATION: Synethetic polypeptide reactant for gas-phase
      analysis

<400> SEQUENCE: 1

Thr Leu Leu Glu Leu Ala Arg
1               5

```
<210> SEQ ID NO 2
<211> LENGTH: 4
<212> TYPE: PRT
<213> ORGANISM: Artificial
<220> FEATURE:
<223> OTHER INFORMATION: Synethetic polypeptide reactant for gas-phase
      analysis

<400> SEQUENCE: 2

Gly Gly Gly Gly
1

<210> SEQ ID NO 3
<211> LENGTH: 4
<212> TYPE: PRT
<213> ORGANISM: Artificial
<220> FEATURE:
<223> OTHER INFORMATION: Synethetic polypeptide reactant for gas-phase
      analysis

<400> SEQUENCE: 3

Met Arg Phe Ala
1
```

PROTEIN/PEPTIDE SEQUENCING BY CHEMICAL DEGRADATION IN THE GAS PHASE

CROSS-REFERENCE TO RELATED APPLICATIONS

Priority is hereby claimed to PCT application Serial No. PCT/US2005/025185, filed Jul. 15, 2005 (and published as WO/2007/015690 on Feb. 8, 2007), which claims priority to U.S. provisional application Ser. No. 60/588,447, filed Jul. 16, 2004, the entire content of both of which are incorporated herein by reference.

FEDERAL FUNDING STATEMENT

This invention was made with United States government support awarded by the following agencies: NIH HV28182. The United States has certain rights in this invention.

FIELD OF THE INVENTION

The invention relates to a method and corresponding apparatus for sequencing polypeptides and proteins in the gas phase using Edman degradation chemistry and mass spectrometry.

BACKGROUND

Proteins are among the most important components of all living systems. Some proteins are hormones; some help defend the body against damage or attack; others act as structural materials of cell walls and membranes, bone and cartilage, hoof and claw. The building blocks of proteins consist of twenty amino acids, linked together by peptide bonds in chains. The diversity in form and function of proteins and peptides stems from the diversity of the amino acid building blocks from which they are made. The twenty naturally-occurring amino acids include side chains that are acidic (Asp and Glu), basic (Lys, Arg, and His), neutral/non-polar (Gly, Ala, Val, Leu, Ile, Phe, Pro, Met), and neutral/polar (Ser, Thr, Tyr, Trp, Mn, Gln, and Cys). The functional nature of a protein is determined by the folded structure that the amino acid polymer assumes. The final three-dimensional form of a protein is largely dependent on its primary structure, i.e. the sequence of the various amino acids along the length of the protein molecule.

Protein Sequencing Technology:

Determining the primary amino acid sequence of any given protein or polypeptide is a formidable task. The first major technology to emerge for the identification of protein sequence is the Edman degradation.[1, 2] The Edman degradation method for N-terminal sequence analysis of proteins has been in use for over 50 years. Since the introduction of the spinning cup sequenator,[3] automated Edman degradation remains the most widely used method for determining the primary structure of proteins. Extensive research has led to progressively more sensitive Edman sequence analysis. Today's state-of-the-art, gas-phase polypeptide sequencers[4] can provide sensitivity at sub-picomole levels. Still, more than 50 years after Edman's initial description of the protocol, the underlying chemistry has remained unchanged: First, a phenylisothiocyanate (PITC) is coupled to the α-amine of the protein or polypeptide to be sequenced. The resulting phenylthiocarbamoyl (PTC) derivative is then hydrolyzed to yield the anilinothiazolinone (ATZ) derivative. The ATZ derivative is then converted in aqueous acid to the more stable phenylthiohydantoin (PTH) (see FIG. 1). In this fashion, the protein or polypeptide target is sequenced, residue-by-residue, starting from the amino terminus of the protein or polypeptide.

In conventional, modern use, the purified protein or polypeptide is applied to glass fiber disks and loaded directly into the reaction chamber cartridge of a gas-liquid solid phase sequencer.[4] If the sample is impure, as is commonly the case, gel electrophoresis is usually used to separate the mixture components. Purified protein sample is then transblotted onto chemically inert membranes, which are then placed in the sequencer for analysis.[5]

In each degradation cycle, reagents and solvents are delivered to the reaction cell under the control of a microprocessor. Polar reagents are introduced in the gas phase to reduce sample loss. After the cleavage step, the N-terminal ATZ derivative is extracted from the reaction cell and delivered into a conversion flask where it is converted to the more stable PTH amino acid. This final product is subsequently analyzed by HPLC. The elution time of the PTH-amino acid derivative is compared with that of standards to identify each residue.

As delicate as current instruments are, there is still a considerable gap between the demands of protein study and the capabilities available for protein sequencing. First, the condensed-phase Edman degradation process is quite slow. For a gas-phase sequencer, each cycle takes 30-60 minutes to complete. Second, the sensitivity of this technique is insufficient to sequence many important proteins that exist in the cell at sub-femtomole or attomole levels. However, the ability to identify individual components has changed drastically with the recent development of new ionization techniques for mass spectrometry.

Bioanalytical Mass Spectrometry:

Mass spectrometry (MS) is an analytical technique that determines the mass of atoms or molecules by means of ion-field (electric or magnetic) interactions. A mass spectrometer consists of three fundamental components: An ionization source, where gas-phase ions are generated; a mass analyzer, where ions of different mass-to-charge ratios (m/z) are separated; and a detector, where the separated ions produce detectable signals.

Ionization Sources: Over the last two decades, the twin techniques of Matrix-Assisted Laser Desorption/Ionization (MALDI) and Electrospray Ionization (ESI) Mass Spectrometry (MS) were developed.[6-8] The two techniques differ significantly but are both highly effective in the production of intact, gas-phase, large biomolecule ions. Producing these ions is a required first step for mass spectrometric analysis.

The success of MALDI is based on the use of a matrix compound that absorbs laser irradiation at a wavelength where the analytes do not. In this technique, the analyte is co-crystallized with a small organic compound. Upon excitation by a laser pulse with sufficient energy density, a sudden and explosive phase transition occurs. From among all the analyte molecules desorbed from the matrix, only a small portion ($\sim 10^4$) are ionized.[9] Although the mechanism of ion formation in MALDI remains in debate,[10, 11] gas-phase proton transfer is generally believed to be involved in this process. Ions produced in MALDI are usually singly-charged, making MALDI amenable to mixture analysis.

Electrospray ionization results in a distribution of multiply-charged ions for each analyte present. The basic ESI source consists of a metal needle maintained at high voltage (~4 kV). The needle is positioned in front of a counter-electrode held at ground or low potential (and which also doubles as the inlet of the mass spectrometer). Sample solution is gently pumped through the needle and is transformed into a mist of micrometer-sized droplets that fly rapidly toward the counter electrode (see FIG. 2). In addition to the applied voltage, a concentric flow of nitrogen is often used to help nebulize the solution and dissolve the analyte ions. As each droplet decreases in size, the field density on its surface increases. When charge repulsion exceeds the force of surface tension, the parent droplet splits into smaller daughter droplets. This droplet fission continues until naked ions are formed.

Mass Analyzers: MALDI and ESI have been coupled to many different mass analyzer types. The two most common are the Time Of Flight (TOF) and the Triple Quadrupole (QqQ).

Time-of-flight (TOF) is the simplest mass analyzer, consisting only of a metal flight tube. The mass-to-charge ratios (m/z) of ions are determined by measuring the time it takes the ions to travel from source to detector. In a TOF measurement, an equal amount of kinetic energy is imparted to the analyte ions by placing them in a strong electric field formed by a large DC potential between two plates. Given that all ions of different ink receive the same kinetic energy ($qV=mv^2/2$), low m/z ions will reach the detector sooner than high m/z ions.

Advantages of TOF MS include the capability to deliver complete mass spectra at high speed and with no mass range limit. The mass-resolving power in TOF measurement is, however, limited by the distribution of initial energy in the analyte molecules and the position of the ions prior to acceleration. Typically, the spatial focusing plane in a single-stage mass spectrometer is only a short distance from the acceleration region (i.e., the apparatus has a relatively short focal length), after which the ions will spread out. A two-stage acceleration system is often utilized to allow spatial focusing at a longer distances from the ion source. The spatial focusing plane can be brought to the detector plane by adjustment of the relative field strength between these acceleration stages. Within a certain mass window, energy focusing can be achieved by the technique of delayed extraction, also known as time-lag focusing. The most successful energy focusing method implemented to date is the "reflectron." In this method, an electrostatic ion mirror (the reflectron) is disposed at the distal end of the flight tube and the electrostatic field within the reflectron is oriented to oppose the acceleration field. Thus, the accelerated ions penetrate into the reflectron, and are ultimately reflected back toward a secondary (or "reflected") focal point. The more energetic ions penetrate more deeply into the reflectron and hence take longer to be reflected back out of the reflectron. Thus the optics can be adjusted to bring ions of different energies to a space-time focus. While the addition of a mirror provides little improvement in theoretical resolution, it dramatically broadens the mass range of focus.[12-14]

A triple quadrupole mass spectrometer is comprised of two mass analyzing quadrupoles (Q1 and Q3) and a radiofrequency-only quadrupole, q2 (see FIG. 3). Quadrupole mass filters can be operated in two basic modes: mass-resolving mode and radio frequency only (RF-only) mode.

In mass-resolving mode, quadrupoles are operated at a constant ratio. The operation points lie on a straight line in a stability diagram, known as the mass scan line (see FIG. 4). When all the experimental parameters are fixed, the mass scan line can be viewed as a collection of points representing particles with different mass-to-charge ratios: heavier ions at the left-lower region and lighter ions at the right-upper region. The portion of the mass scan line that is intercepted by the boundary of the stable region represents a transmission window. Only m/z ratios that fall into this window will be transmitted. The length of this segment defines the resolution of transmission.

In RF-only mode, the DC voltage is removed. The mass scan line in this case coincides with the q axis. The transmission window is now between the m/z of infinity and the low-mass cut-off value. This operation mode is also known as the high-pass mode.

In a QqQ MS, the RF-only quadrupole (q2) functions as a collision cell in which the buffer gas pressure is maintained at about from 1 to about 119 mTorr. Precursor ions selected by Q1 enter the RF collision quadrupole, q2, where they undergo collision-induced dissociation. Product ions are then mass filtered by scanning the third quadrupole, Q3, to produce the product mass spectrum.

Ion Detectors: The most commonly used ion detectors are electron multiplier detectors, including channel electron multipliers (CEM) and microchannel plate detectors (MCP). These detectors operate by means of secondary electron generation. Initial secondary electrons generated upon impact of incident ions start an electron avalanche that produces an output signal. Because the response of electron multiplier detectors to ions with a fixed kinetic energy falls off significantly with increasing mass, ion detectors based on different detection mechanisms have been developed. One strategy is to detect the charge directly. Briefly, as ions approach the detector, image charges are formed on the surface of the detector, which are then picked up by an external circuit generating an output signal. The major limitation in this detection scheme is the low sensitivity due to the lack of inherent amplification.[15] In another approach, the energy deposited in a suitable material by impact of an ion can be detected.[16-24] Using two superconducting layers separated by an insulating layer, ions that strike the detector create non-thermal phonons (lattice vibrations). Phonons with sufficiently high energy can break the weakly bound electron pairs (Cooper pairs) in the superconducting layer, which results in a measurable tunneling current through the insulating baffler. These detectors are more efficient than MCP's, especially for detecting large ions. However, these types of detectors require liquid helium cooling and generally have a small active area, which limits their use in routine applications.

SUMMARY OF THE INVENTION

Despite the success of protein sequencing methods based on electrophoretic technologies, there remains the potential for even greater improvement through mass spectrometric (MS) analysis methods, as disclosed and claimed herein. In contrast to electrophoretic mobility, which is an extrinsic and highly condition-dependent property of molecules, mass-to-charge ratio (m/z) is an intrinsic and condition-independent property of ions. Therefore, an m/z ratio determined on a mass spectrometer is an intrinsically more accurate and dependable parameter for the analysis of a molecule than is electrophoretic mobility. Moreover, the speed of MS analyses is truly phenomenal, with the potential for analyses to be completed on a millisecond scale. Thus, by developing MS methods for amino acid sequencing that are suitably robust and high-performance, mass spectrometric-based methods have the potential to transform quite radically the nature of large-scale polypeptide and protein sequencing efforts. Finally, whereas electrophoresis-based methods are fairly mature at the present time, with only the potential for a variety of incremental improvements within the existing paradigm, MS-based methods present a wholly new approach to protein and polypeptide sequencing.

Mass spectrometric (MS) approaches to protein sequencing fall into three general categories. The first approach is to replace fluorescence detection with MS detection for gel electrophoresis. This approach is comparatively straightforward, but does not eliminate gel electrophoresis from the sequencing process. The second approach is to replace gel electrophoresis with laser fluorescence, a more robust detection method. The third approach (and the focus of the present invention) is to introduce an intact polypeptide or protein molecule into a mass spectrometer, to fragment the molecule, and then to determine the primary amino acid sequence of the molecule via mass spectral analysis of the fragments. This method is an enormous advancement over prior art amino acid sequencing methods.

Due to the MALDI and ESI ionization techniques, the analysis of proteins by mass spectrometry has emerged as the technique of choice for obtaining high performance results from small amounts of analyte. There are several basic approaches to de novo protein sequencing where mass spectrometric techniques are involved.[25] In one approach, mass spectrometry is simply introduced as a detection system. HPLC fractions of Edman degradation products are analyzed by a mass spectrometer in place of the conventional UV detector. Although the sensitivity has been pushed down to the high attomole level by using this method, the sequencing speed is not increased at all. In another approach, a concentrated set of peptide fragments (a sequencing ladder) is generated, either chemically or enzymatically, in a controlled fashion. The sequencing ladder is subsequently separated and detected by a mass spectrometer. This protein ladder sequencing technique lends itself to very high sample throughput at very low per-cycle cost. Disadvantages of this technique include the lengthy sample preparation and the large amount of pure peptide required.

Protein/peptide sequence information can also be obtained by tandem mass spectrometry.[26, 27] In the tandem MS approach, protein is first digested into peptide fragments with an enzyme. This mixture is subsequently introduced into the ion source of a mass spectrometer, either directly or after separation by liquid chromatography. Precursor ions, selected by a first mass analyzer, are fragmented by collision-induced dissociation (CID) or post-source decay (PSD). The resultant fragments are then analyzed by a second mass analyzer. Interpretation of the MS/MS data allows for the partial or complete elucidation of the peptide sequence so as to piece together a more complete sequence of the protein.

More often, MS acts as a powerful tool for identification of known proteins. The protein of interest is first digested by a proteolytic enzyme and analyzed by mass spectrometric techniques. The mass spectra of intact peptides constitute a "peptide mass fingerprint" (PMF) unique to the protein digested.[28] The PMF obtained is subsequently compared to "virtual" fingerprints derived by theoretical cleavage of protein sequences stored in a database. The protein of interest is identified when a match is found. Alternatively, the peptide mixture from protein digestion (usually by trypsin) is fractionated by either gel electrophoresis or liquid chromatography methods, the fractions of which are then analyzed by tandem MS. Subsequently, the information created by the CID of peptides is used to search a protein database for a match within the expected MS/MS data from the known tryptic peptides.

The field of mass spectrometry has developed significant bioanalytical capacity with the recent development of the twin ionization techniques: MALDI and ESI. The promise for rapid and accurate sequence analysis of proteins by mass spectrometry, however, is limited by the decreased sensitivity with increasing lengths of the polypeptide chain. The mass spectrometric approaches based on database searching have become the method of choice in high-throughput identification of known proteins. These methods, however, will not work if the protein in question is not in a protein database. In short, if the mass spectrum of the protein analyte does not yield a match within the database, the protein cannot be sequenced by conventional mass spectrometric means. Therefore, the present invention is directed to a novel protein/polypeptide sequencing technique based on gas-phase Edman degradation. This technique disclosed herein provides matchless speed and sensitivity for de novo sequence analysis of intact proteins and peptides.

The development of rapid and sensitive methods to obtain sequence information of protein and peptides remains an active area of research both in solution and in gas phase. Currently, sequence analysis of proteins is done using the Edman degradation to generate N-terminal PTH derivatives, whose identity is then determine using any number of methods (including mass spectrometry). Note that in the conventional, automated Edman approace, MS is used solely as a means for detection. In the conventional approach, the Edman degradation reaction does not take place within the mass spectrometer itself.

Mass spectrometry can be coupled to Edman degradation in several different ways. One approach is to use MS to replace the conventional UV detection at the end of each Edman degradation cycle.[29] As noted above, while this approach provides sensitivity at high attomolar level, there is no gain in sequencing speed. Another approach is to generate sequencing ladders consisting of degradation fragments of different lengths. These ladders, which are subsequently separated in size and detected in the mass spectrometer,[30] provide higher sample throughput but the approach still requires a fair amount of up-stream wet chemistry. The need for this additional processing limits further improvement in the sensitivity and speed of sequence analysis.

In contrast to these two approaches, in the present invention an intact protein or polypeptide molecule is introduced into a mass spectrometer and allowed to accumulate in a linear ion trap. Edman degradation reactions are then conducted in gas phase (within the linear ion trap) by introducing chemical reagents into the ion trap. The cleavage products after each cycle are then ejected/extracted from the ion trap and their mass spectrum is determined. Note that when the Edman degradation is performed in this fashion, the final conversion step used on condense-phase sequencing (where the ATZ derivative is converted in a PTH derivative; see FIG. 1) is unnecessary because there is no mass change involved in the conversion. This is the most ambitious of the three approaches, and is the focus of the present invention. The invention thus combines the time-tested de novo sequencing capability of Edman degradation chemistry and the speed and sensitivity of mass spectrometry.

N-terminal derivatization of peptides with phenylisothiocyanate and related derivatization reagents, followed by collision-induced dissociation of the resulting phenylthiocarbamoyl derivative, results in the selective formation of modified thiazolone $b_1$ ions. While not being limited to any specific mechanistic pathway, the proposed mechanism for the fragmentation of PTC derivatives of protonated peptides to yield modified $b_1$ and complementary $y_{n-1}$ ions[31] closely resembles the now-accepted mechanism for b-ion formation of protonated peptides (see FIG. 5).

In the invention disclosed and claimed herein, gas-phase coupling reactions and cleavage reactions analogous to the first two steps in condensed-phase Edman degradation were studied separately for small peptides using a modified triple quadrupole mass spectrometer. Methylisothiocyanate (MITC) was used as the gas-phase Edman reagent. Selective cleavage of the N-terminal peptide bond of the peptide derivative ion was achieved by collisional induced dissociation. As described below, gas-phase Edman degradation is a promising approach for sequence analysis of intact protein/peptides.

The primary embodiment of the invention is thus a method of identifying an amino acid residue of a polypeptide or protein. The method comprises performing a peptide degradation reaction on a polypeptide or protein ion reactant in the gas phase. The reaction yields a first ion product corresponding to a first amino acid residue of the polypeptide or protein reactant, as well as a polypeptide or protein fragment ion. The mass-to-charge ratio for the first ion product, or the polypeptide or protein fragment ion, or both is then determined. Lastly, the first amino acid residue of the polypeptide or protein reactant is identified from the mass-to-charge ratio so determined.

The method can be repeated reiteratively to determine part or all of an amino acid sequence of the polypeptide or protein reactant.

It is preferred that the polypeptide or protein reactant is ionized via electrospray ionization. Other ionization methods can also be used, such as matrix-assisted laser desorption/ionization.

Additionally, the peptide degradation reaction can be performed on a plurality of different polypeptide or protein reactants simultaneously. Here, the reaction yields a corresponding plurality of first ion products and a corresponding plurality of polypeptide or protein fragment ions. The mass-to-charge ratios for the corresponding plurality of polypeptide or protein fragment ions is then determined. In this fashion, the first amino acid residue of each polypeptide or protein reactant in the plurality can be determined from the mass-to-charge ratios so determined.

Another embodiment of the invention is directed to a method of determining an amino acid sequence of a polypeptide or protein. The method comprises performing a gas-phase peptide degradation reaction on a polypeptide or protein reactant within an ion trap, wherein the reaction yields a first ion product corresponding to a first amino acid residue of the polypeptide or protein reactant. The first ion product is then selectively transmitted from the ion trap into a mass spectrometer. The mass-to-charge ratio for the first ion product is thus determined and the chemical identity of the first amino acid residue of the polypeptide or protein reactant is also determined (preferably by comparison to known standards). The steps are then repeated to determine part or all of the amino acid sequence of the polypeptide or protein reactant.

More specifically, the invention includes a method of determining an amino acid sequence of a polypeptide or protein, where the method comprises ionizing a polypeptide or protein reactant to yield a reactant ion and then trapping the reactant ion within a linear ion trap. The polypeptide or protein reactant is then contacted with an Edman reagent to yield a thiocarbamoyl intermediate. The intermediate is then subjected to collision-induced dissociation, or contacted with an acid, to yield a first ion product. The first ion product is then selectively transmitted into a mass spectrometer to determine its mass-to-charge ratio. A chemical identity for the first amino acid residue of the polypeptide or protein reactant is determined based on the mass spectrum so generated.

The invention is also directed to a mass spectrometer comprising: an ion trap comprising a quadrupole having selectively adjustable voltage and radio frequency, an entrance having selectively adjustable voltage, and an exit having selectively adjustable voltage, wherein the ion trap is dimensioned and configured to allow gas-phase reactions to take place therein. The spectrometer includes a valve operationally connected to the ion trap, wherein the valve is dimensioned and configured to introduce reagents into the ion trap. Lastly, the device comprises a quadrupole mass analyzer operationally connected to the exit of the ion trap.

Another embodiment of the invention is a mass spectrometer that comprises a linear ion trap. The linear ion trap comprises a quadrupole cell having a plurality of segments, wherein voltage and radio frequency within each segment is selectively adjustable independent of all other segments. The linear ion trap further comprises an entrance having selectively adjustable voltage and an exit having selectively adjustable voltage. The linear ion trap is dimensioned and configured to allow gas-phase reactions to take place therein. A valve is provided to introduce reagents into the ion trap. A charge reducer is operationally connected to the entrance of the ion trap. A quadrupole mass analyzer is operationally connected to the exit of the ion trap, and an orthogonal time-of-flight mass analyzer is operationally connected to the quadrupole mass analyzer.

BRIEF DESCRIPTION OF THE DRAWINGS

FIGS. 8A and 8C depict the image charge formed on the detection electrode of an inductive detector as a function of time. FIGS. 8B and 8D illustrate the output voltage generated upon detection of negative and positive ions, respectively. The time points t=t±1 correspond to the time when the ion is at the front and rear of the detector, respectively; t=0 corresponds to when the ion is at the plane of the detection grid.

FIG. 15A: singly-charged MRFA. FIG. 15B: doubly-charged MRFA. FIG. 15C: singly-charged TLLELAR. FIG. 15D: doubly-charged TLLELAR.

DETAILED DESCRIPTION OF THE INVENTION

Figure 1:
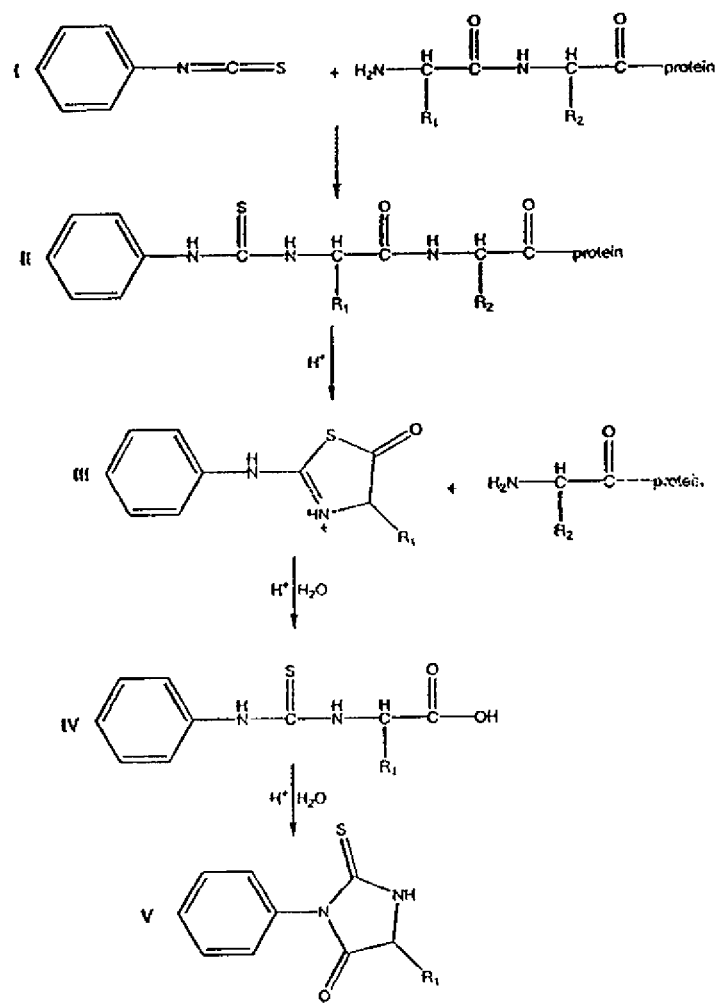
FIG. 1 is a reaction scheme depicting the sequential steps in conventional Edman degradation reaction. Step I is the reaction of a phenylisothiocyanate (PITC) with the N-terminal residue of the protein to be sequenced. Step II shows the formation of a phenylthiocarbamoyl (PTC) intermediate. Step III illustrates the formation of the anilinothiazolinone (AZT) residue. Steps IV and V illustrate the conversion of the AZT residue into a more stable phenylthiohydantoin (PTH) derivative.
Figure 2:
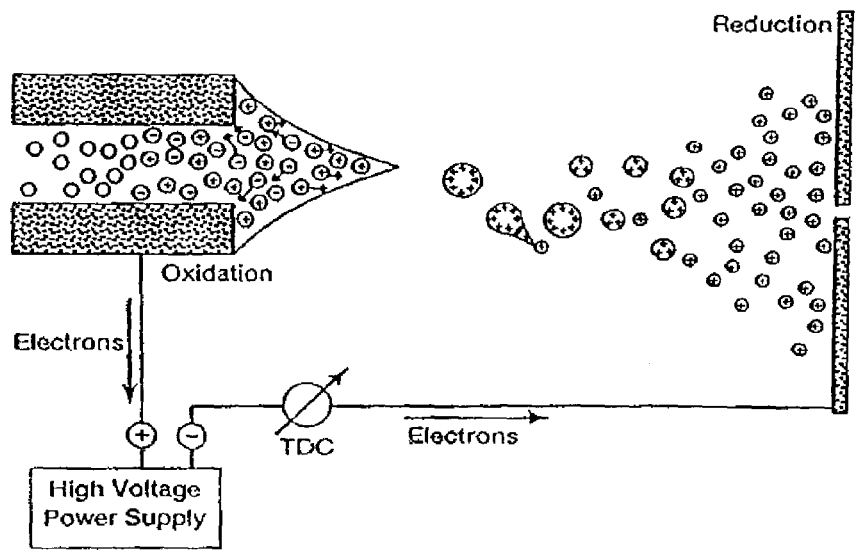
FIG. 2 is a schematic drawing illustrating electrospray ionization (ESI). The very high electric field imposed by the power supply causes an enrichment of positive electrolyte ions at the meniscus of the solution at the metal capillary tip. The net positive charge is pulled downfield by a negatively-charged electrode, thereby transforming the meniscus into a cone that emits a fine mist of positively-charged droplets. Solvent evaporation reduces the volume of the droplets (which maintain their constant charge), which causes the droplets to fission. Charge balance is attained by electrochemical oxidation at the positive electrode and reduction at the negative electrode.
Figure 3:
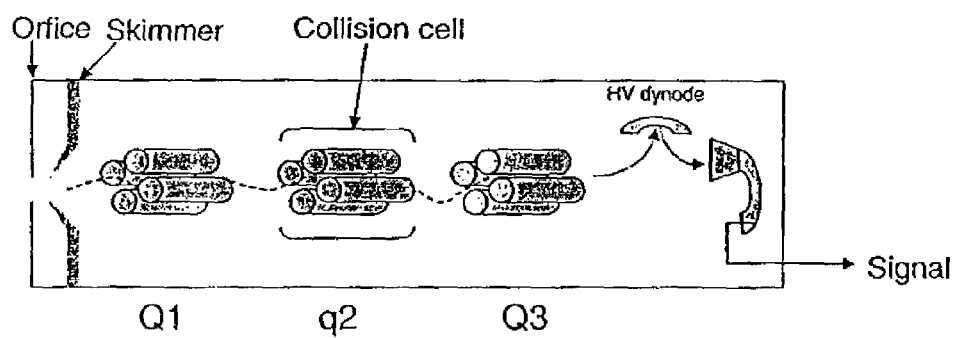
FIG. 3 is a schematic diagram of a triple quadrupole mass spectrometer. Q1 and Q3 are mass-analyzing quadrupoles and q2 is a radio frequency-only (RF-only) quadrupole.

The method disclosed provides a new technology for protein sequencing with high speed and sensitivity. While the washing and extraction steps in condensed-phase Edman degradation are lengthy and troublesome, manipulation of gas-phase ions is clean and fast. Moreover, the conversion step can be skipped in gas-phase degradation because it is the mass of the product ions that is measured. The sensitivity in conventional Edman degradation is mainly limited to the high femtomole level (300-500 fm). Mass spectrometry is capable of detecting $10^5$ ions with microchannel plate detectors, which expands the sensitivity to the attomole level. Therefore, sequence information can be obtained for literally any protein spot detectable on a gel.

The following definitions apply herein. For those terms not given an explicit definition, the art-accepted meaning of each term within the field of mass spectrometry is intended.

The terms "detector," "charge detector," "ion detector," and the like are used synonymously herein. A "detector" is any device, without limitation, now known or developed in the future, that can detect ions. Explicitily included within the term "dectector" are channel electron multipliers (CEMs), microchannel plate detectors (MCPs) and inductive ion detectors.

The term "Edman reagent" refers broadly to any compound capable of being used in the Edman degradation reaction to sequence polypeptides and proteins. The term "Edman reagent" explicitly encompasses isothiocyanate-containing compounds, including, without limitation, substituted and unsubstituted alkyl-isothiocyanates (e.g., methylisothiocyanate, ethylisothiocyanate, etc.), and substituted and unsubstituted aryl-isthiocyanates (e.g., phenylisothiocyanate, halo-substituted phenylisothiocyanate, etc.). See Table 1. A host of different Edman reagents can be purchased from suppliers such as Sigma-Aldrich Chemicals, Milwaukee, Wis.

The term "ion" refers to singly- or multiply-charged atoms, molecules, and fragments of molecules, or either positive or negative polarity. The term "ion" also encompasses charged aggregates of one or more molecules or fragments or molecules.

The terms "ionization source," "ion source," or "ionizer" are used synonymously herein. These terms denote any device, without limitation, now known or developed in the future, that generates ions. Explicitly included are matrix-assisted laser desorption/ionization (MALDI) and electrospray ionization (ESI) device. Other types of ionizers include laser-induced ionization (in the condensed or liquid phases), corona discharge ionizers, and the like.

The terms "mass spectrometer" or "mass analyzer" define any device used to determine the mass-to-charge ratio (m/z) of an ion in the gas phase. Examples include, but are not limited to, time-of-flight mass spectrometers, quadrupole mass spectrometers, and tandem and multi-stage mass spectrometers.

The term "operationally connected" when referring to two or more elements of a device indicates that the two elements communicate with one another (directly or indirectly, physically, electronically, electrically, or via a wireless connection, etc.) and function as defined with respect to one another. Elements that are "operationally connected" do not need to be physically or directly connected to one another.

The term "selectively adjustable" indicates an ability to select the value of a parameter over a range of possible values. As applied to certain aspects of the present invention (such as voltage or frequency settings), the value of a given selectively adjustable parameter can take any one of a continuum of values over a range of possible settings. Unless explicitly stated to the contrary, all machine settings referenced in the disclosure are selectively adjustable.

Figure 6:
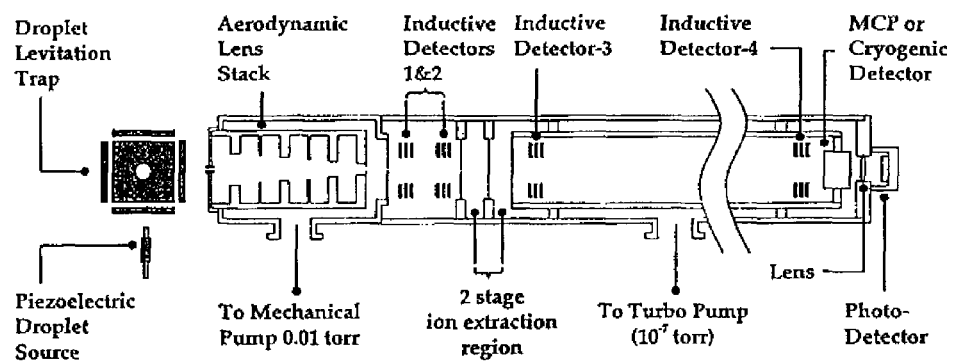
FIG. 6 is a schematic diagram of a mass spectrometer.

A schematic diagram of a first embodiment of a mass specrometer according to the present invention is shown schematically in FIG. 6. The instrument shown in FIG. 6 utilizes time-of-flight mass analysis of large ions generated from individual charged droplets. Charged droplet production is accomplished with a piezoelectric droplet-on-demand dispenser. The charged droplet is held in an electrodynamic trap to desolvate. Once a trapped droplet reaches the desired state of desolvation, it (or the resultant gas-phase analyte ion) enters the high vacuum region of the mass spectrometer via an aerodynamic lens. The aerodynamic lens sub-assembly functions to focus the analyte droplet or ion onto a central axis where an in-line TOF mass analysis is subsequently performed. A series of inductive detectors are employed along the TOF axis to measure both the ion's initial velocity and the velocity after TOF acceleration to yield an accurate mass. The nondestructive nature of this new ion detection scheme allows further ion detection using more sensitive detectors or tandem MS to be performed.

Pulsed nanoelectrospray sources have been developed in the Lloyd Smith group at the University of Wisconsin-Madison. See U.S. Pat. No. 6,906,322, issued Jun. 14, 2005, to Berggren, Westphall & Smith, and U.S. Pat. No. 6,797,945, issued Sep. 28, 2004, to Berggren, Westphall, Scalf & Smith (the entire contents of which are incorporated herein). The ion source is constructed from a glass capillary epoxied into a cylindrical piezoelectric element. A single droplet is released from the end of the capillary as a result of a rapid pressure pulsation generated by a radial contraction of the piezoelectric element. The size of the droplet produced depends on the solution conditions, the orifice diameter, and the amplitude and duration of the pressure pulse which is controlled by the amplitude, duration and shape of an electronic pulse applied to the piezoelectric element. The droplets are charged by inserting a platinum wire into the back end of the dispenser to hold the solution at high potential. On one hand, the ability to control the number and frequency of ionization pulses distinguishes this ionization technique from continuous ionization sources like ESI. On the other hand, this technique has the advantages associated with the gentle nature of ESI, while avoiding the undesirable characteristics of the mutual charge repulsion leading to inefficiencies in sample introduction.

Referring to FIG. 6 generally, the droplets generated using the piezoelectric ionization source are often too large (~20 μm in diameter) to be completely desolvated before entering the high vacuum region of the mass spectrometer. Therefore a device is needed to extend the desolvation time. An electrodynamic droplet levitation trap accomplishes this task. The charged droplet is retained in the levitation trap until it has neared complete desolvation (i.e., until the drop reaches the same size as ESI-generated droplets, generally 0.1 μm or less) at which point the droplet will exit the trap and be guided into the entrance port of the mass spectrometer by an aerodynamic lens.

An aerodynamic lens assembly comprising of a series of apertures with decreasing size, replaces the conventional nozzle-skimmer and collisional cooling regions used in typical ESI instruments. Electrostatic lenses are often employed to collimate or focus an ion beam through apertures. However, most lens systems exhibit aberrations of one type or another, such as minimizing the optimum focus conditions to a narrow ink window over a limited energy range. Furthermore, ions that are brought into focus through an aperture will quickly diverge on the far side of the aperture. The aerodynamic lens stack[59-62] has the unique capability of being able to direct a droplet or particle, in the sub-micron size range, through a nozzle skimmer arrangement which exits into a region of high vacuum with the particle exiting on axis. The lens stack utilizes the flow of a background gas (going from a region of higher pressure to a region of lower pressure) in place of electric potentials to transport and focus the ion. The charged droplet is brought to the center axis due to its inertia, rather than its charge.

Inductive ion detectors have been developed for TOF measurement and can be used as detectors in the present invention.[15, 41, 63-65] An inductive detector measures an image charge created on a conductive surface as the ion passes by the surface. The velocity of the ion can thus be determined from the timing information obtained as it passes through two inductive detectors with known separation.

Figure 7:
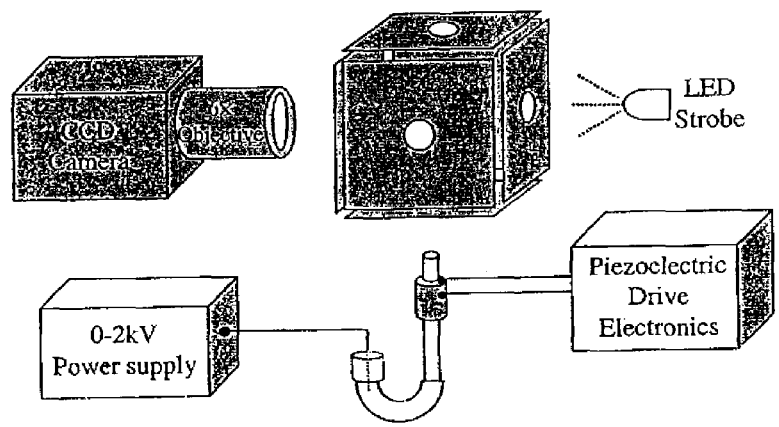
FIG. 7 is a schematic diagram of a cubic electrodynamic trap and related components.
Figure 8A:
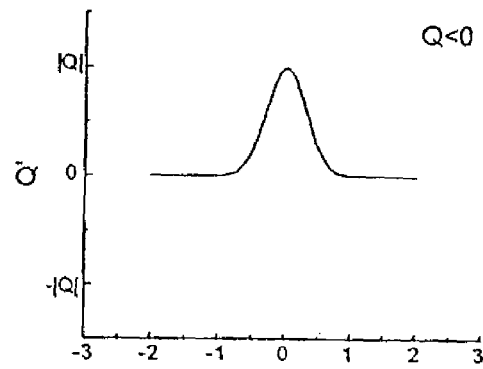
FIGS. 8A, 8B, 8C, and 8D are graphs showing image charge (Q') or output voltage (Vout) as a function of time.
Figure 8B:
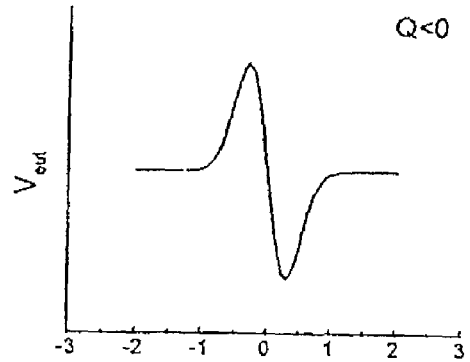
Figure 8C:
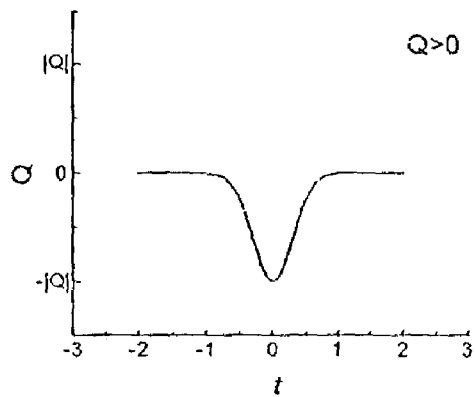
Figure 8D:
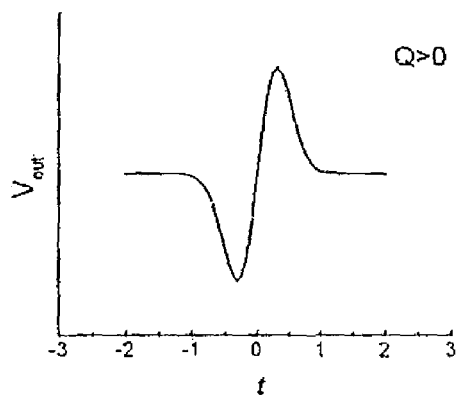

Electrodynamic droplet levitation has characteristics that interface nicely with the mass spectrometer disclosed herein; namely, the ability to direct the desolvated droplet, or its offspring daughter droplets, out of the trap along a defined axis. A cubic trap, illustrated schematically in FIG. 7, is preferred.

The basic principles of a cubic trap are as follows. The opposing faces of a cube constitute three sets of planar electrodes, that is, each pair of opposing faces is an electrode set. Each set of planar electrodes is driven by an AC voltage which is 120° out of phase with the other two. Alternatively, two sets of planar electrodes may be driven 60° out of phase while the third set is held at ground. In either case, a DC potential may be applied to a set of electrodes to generate a balance force between the plates. Both plates in the electrode pair are driven with the same AC signal. An aperture located in the center of the planar electrode allows access to the trap and is reported to have negligible effect on the electrodynamic characteristics of the trap for aperture diameters less than one eighth the length of the side of the planar electrode. (A circular aperture is preferred; apertures of other geometries can be utilized, provided they are suitable small so as not to disturb the electric fields generated by the electrodes.)

The motion of a particle inside the trap can be described by $$d^2u/dt^2+(6\pi\eta r/m)du/dt-(q/m)E_u=0 \qquad (1)$$

where μ represents any of the three axial displacement variables x, y and z. Eμ is the AC component of the electric field, η is the viscosity of the medium in which the particle is immersed, q is the charge on the particle and r is the radius of the particle. A simplified expression for the electric field inside the cubic trap (which is accurate only near the center of the cube) is:

$$E_u=(8.3212/a)(u/a-0.5)Vac-\cos(\omega t) \qquad (2)$$

where a is the edge length, Vac is the peak amplitude and ω the frequency of the AC voltage. Substituting Equation 2 into Equation 1, and making the following changes of variables:

$$U=u-a/2,\ \omega t=2,\ 2K=(12\pi\eta r)/(\omega m),\ 2Q=33.248qVac/(\omega m^2 a^2)$$

equation 1 can be rewritten as $$d^2U/d\tau^2+2K(dU/d\tau)-2Q(\cos 2\tau)U=0 \qquad (3)$$

Figure 4:
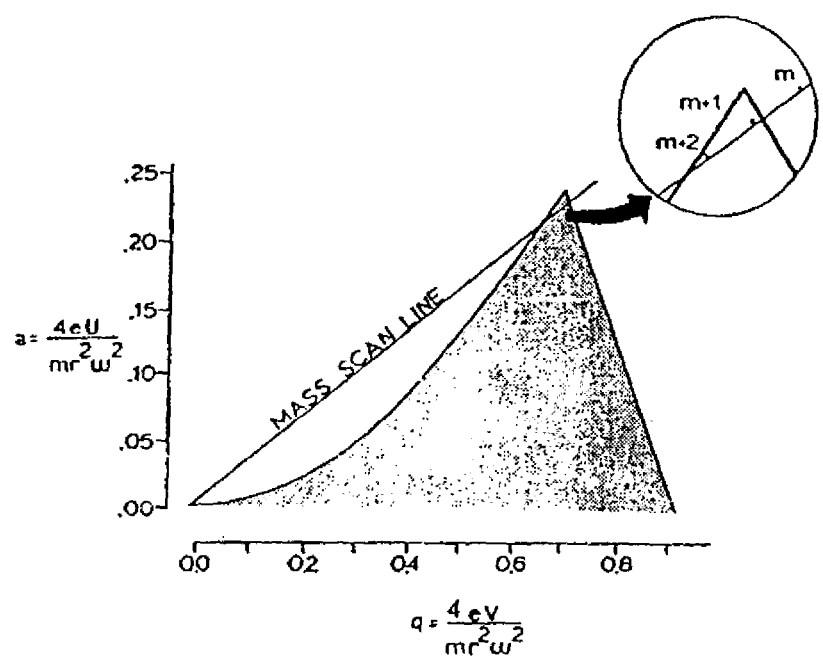
FIG. 4 is a typical a-q stability diagram. The shaded area represent those areas in a-q space wherein correspond to stable solutions of Mathieu's differential equation. The amplified portion shown in the circle indicates that ions of m/z=m+1 and m+2 fall within the stability diagram (thus indicating that the quadrupole filter functions as a two a.m.u. bandpass mass filter.[56]
Figure 5:
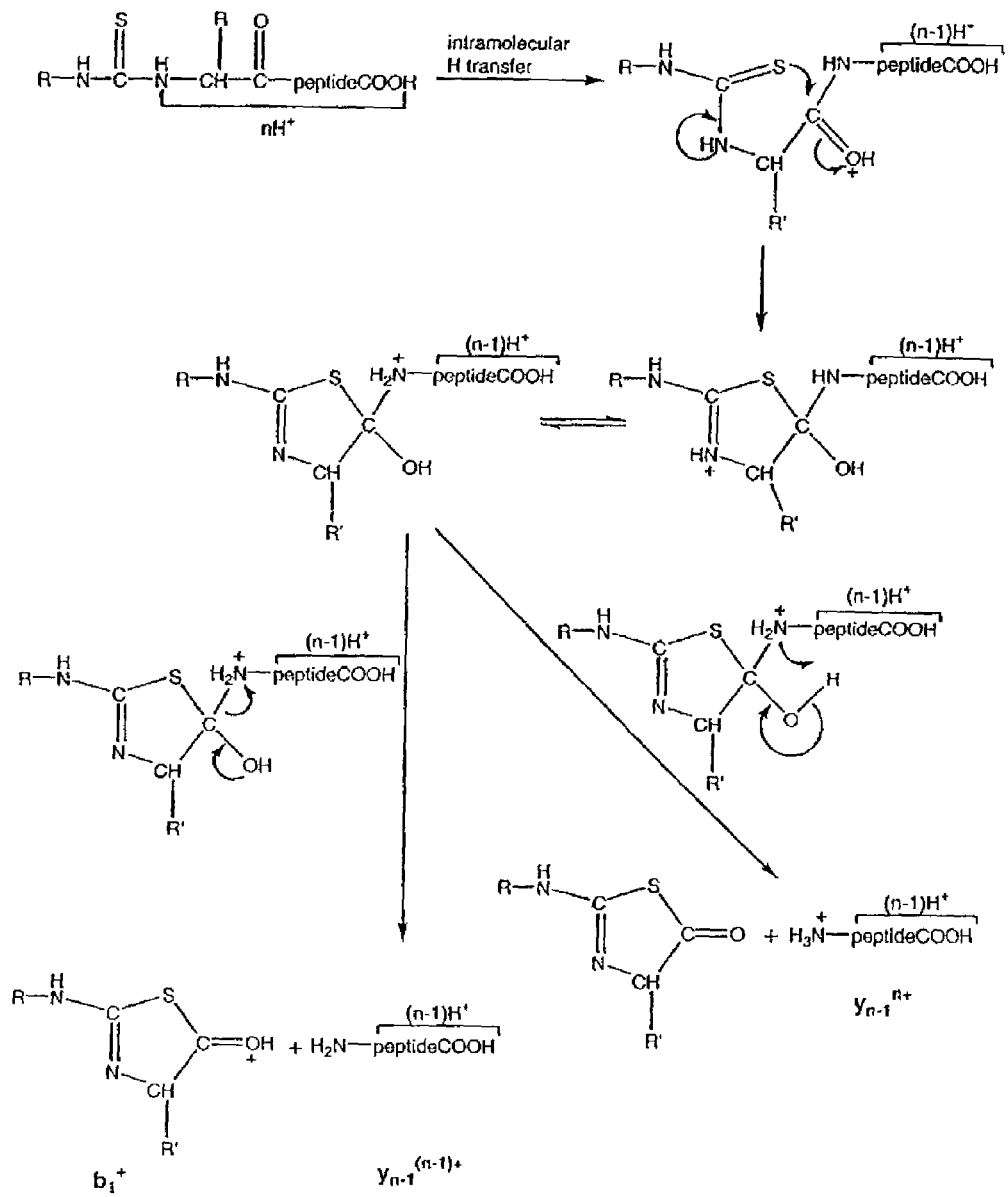
FIG. 5 is a reaction scheme illustrating the generally accepted mechanism for the fragmentation of thiocarbamoyl derivatives of protonated peptides to yield modified $b_1$ and $y_{n-1}$ ions.[31]

Equation 3 is a damped form of the Mathieu differential equation. This particular differential equation also describes the motion of an ion in a multipole field. Recall that the solution to this equation defines the stability region; see FIG. 4. Given a certain combination of ω and Vac, only particles within the stability region (i.e., particles with a certain range of size, mass and charge) will be trapped. A droplet within the stability region, but initially not at the center of the trap will be brought into a stable oscillation in the central region of the trap and oscillate at the frequency of the AC signal applied to the electrodes.

A point of interest about the trap is that a droplet with enough energy to enter the trap will also have enough energy to exit the trap if the droplet were able to maintain its energy. However, the viscous drag force due to air molecules within the trap removes energy from the droplet, thereby permitting it to obtain a stable trajectory inside the trap.

FIG. 7 shows a schematic diagram of a typical experimental setup. A droplet dispenser is employed to introduce droplets into the trap. Charged droplets are formed by applying +1 kV to the solution electrode in the dispenser. The droplet dispenser can dispense a single charged droplet or produce charged droplets continuously at low frequency (~1 Hz) as controlled by the frequency of the voltage pulses applied to the piezoelectric element.

The preferred cubic electrodynamic trap is constructed from six thin copper plates. Each plate has an edge length of 2.54 cm and a center aperture that is 0.32 cm in diameter. Two non-conductive square frames are used to hold the six copper plates in position and separate them from each other. One pair of opposing plates are first embedded into frames, the other four plates, perpendicular to the two embedded plates, are then inserted into the four sides of each frame. Each pair of opposing plates are separated by 2.79 cm. The pair of electrodes perpendicular to the vertical direction are referenced to ground, while the other two pairs are connected to AC voltages 60° out of phase.

The cubic trap drive electronics are briefly described as follows: Two sine waves are generated by a programmable analog voltage output device (National Instruments (Austin, Texax), Model PCI-6173). The sine wave frequency, amplitude, and phase shift are all software controllable. The output signals with maximum peak-to-peak amplitude of 20 V is fed into step-up transformers to produce the high voltage AC signals of several hundred to several thousand volts (peak-to-peak). The output signals from the transformers are AC coupled to DC high voltage converters which provide DC offset voltages to the electrode pairs. The high voltage DC offsets (0-200 V) can be regulated via analog signals (0-12 V) from the PCI-6713 board.

The size of a trapped droplet is measured from the image acquired using a CCD camera attached to a 6× microscope objective. A single CCD pixel corresponds to an area of 16 $\mu m^2$. From the pixelized image, the droplet diameter can be measured. The error associated with the measurement is ±4 $\mu m$ based on the size of the individual pixels comprising an image. The droplets are illuminated by an LED strobe driven at the same frequency as that of the electrodynamic trap (typically 60 Hz). The initial size of a droplet as it is formed at the dispenser tip is measured in a similar manner by moving the CCD camera and the LED strobe from the central region of the trap to the dispenser tip. For droplet initial size measurements, the LED strobe is coupled to the droplet dispenser, that is droplets are generated continuously at the same frequency (~1 Hz) as that of the LED strobe. During these measurements, a mechanical shutter is employed to block these droplets from entering the trap. In trapping experiments, the shutter is removed, and the operational mode of the dispenser is switched from continuous droplet generation to single droplet generation.

Detection by charge induction (i.e., inductive ion detection) can eliminate some of the problems associated with a MCP detector. First, high abundances of low-mass ions will not affect the response of the detector to later-arriving ions. Second, the detection efficiency of the inductive detector should not be affected by ion velocity or mass. Finally, inductive detectors need not destroy ions in order to detect them, which makes it possible to use the ions in subsequent experiments (e.g. coincidence detection, or tandem mass spectrometry).

In the following discussion, the inductive detector was positioned at the end of a TOF mass spectrometer and aligned with the ion beam axis. All spectra were obtained at an acceleration voltage of 25 kV.

A charge sensing grid detector was constructed which resembles that described by Park et al.[63] The detector comprised three 90% transmission grids (MN-17, InterNet, Inc., New Hope, Minn.) applied to thin stainless steel rings using silver print (GC/Waldom Electronics, Inc., Rockford, Ill.). The steel rings have an outer diameter of 6.99 cm and an inner diameter of 5.08 cm. The grids are placed parallel to one another with the distance between adjacent grids being 0.57 cm. The inner grid is the detection grid and the two outer grids are shielding grids. The outer shielding grids are held at ground, while the center detection grid is connected to the gate of a 2N4416 FET.

When a positive ion is being detected, there will be no induced charge on the detection grid when the ion is outside of the detector. As the ion enters the detector, negative image charge is created; that is, electrons are drawn from external circuit to the detection grid causing a current flow, I(t). The magnitude of the negative image charge, Q', increases as the positive ion moves closer to the detection grid, reaches a maximum of Q when the ion is at the plane of the detection grid, then decreases as the ion moves away from the detection grid. The current flow, I(t) is related to Q' by the equation I(t)=dQ'/dt. The current flowing from the detector to the gate of the FET flows through a feedback resistor, Rf, producing an output voltage, Vout. Vout can be calculated by Vout=I(t) Rf.

The image charge, Q', and the output signal, Vout, generated upon detection of both positive and negative ions, are illustrated in FIGS. 8A, 8B, 8C, and 8D as functions of time. In FIGS. 8A-8D, t=±1 corresponds to the time when the ion is at the plane of the back and front shielding grid, respectively, and t=0 when the ion is at the plane of detection grid. Notice the bipolar nature of Vout and the difference in polarity between responses to positive and negative ions.

To eliminate any unwanted signals produced by secondary electron emission and secondary ion generation, the transmission grids are removed from the charge sensing grid detector. The converts the induction detector into charge-sensing ring detector since it comprises three ring electrodes as the shielding and detection elements.

Figure 9A:
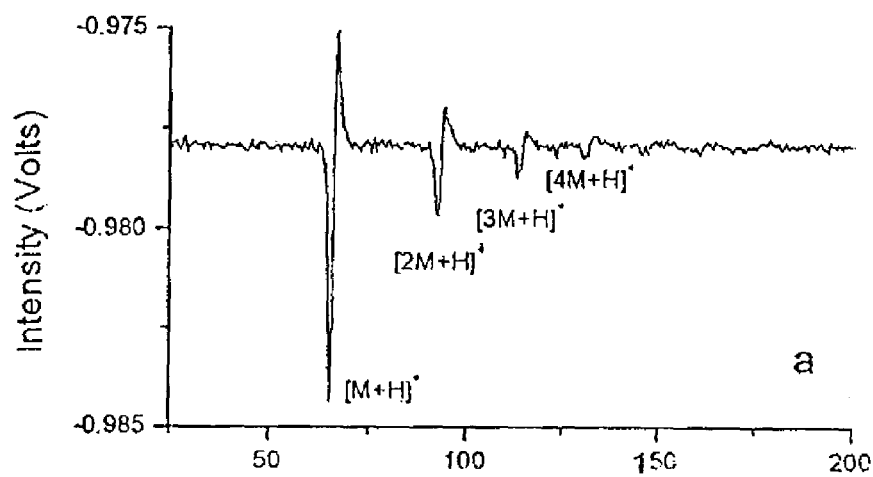
FIG. 9A is a mass spectrum of insulin (100 µM) acquired with a charge-sensing ring detector in positive ion mode.
Figure 9B:
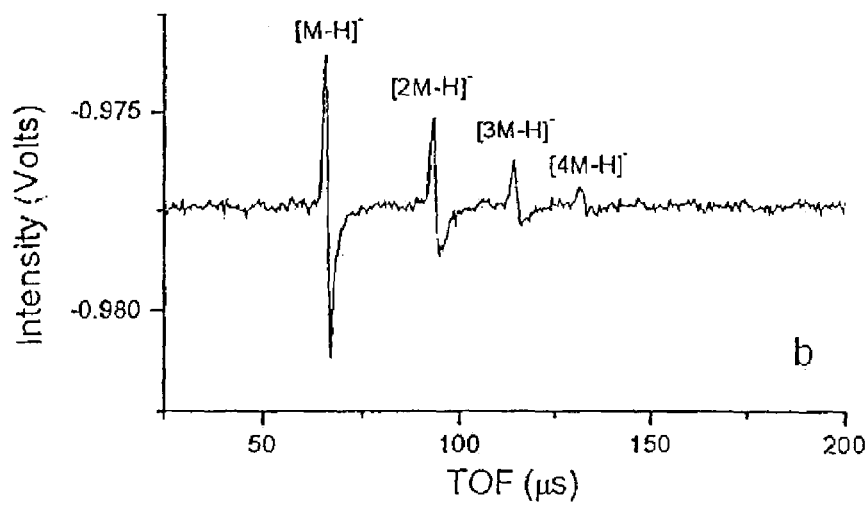
FIG. 9B is a corresponding mass spectrum acquired with the ring detector in negative ion mode.

FIGS. 9A and 9B show representative MALDI-TOF spectra of insulin acquired in both positive-ion mode and negative-ion mode (respectively) with a charge-sensing ring detector. Comparing FIGS. 9A and 9B with FIGS. 5A-8D indicates that the response of the charge-sensing ring detector is indeed due to image charge formation. Note that FIGS. 9A and 9B are mirror images of one another, clearly revealing the reversal of polarity between the two spectra.

The effects of a number of parameters upon the performance of this detector were investigated. This type of detector has an inherent peak broadening effect due to the separation between the shielding ring and the detection ring. For this reason, the distance between adjacent rings was decreased from 0.57 cm to 0.25 cm to improve the resolution. Another geometry factor, the inner diameter of the rings, has a direct impact on the total image charge induced. For an ion traveling on center axis, image charge formation is more efficient when smaller rings are used because the ion passes closer to the detection electrode. However, larger rings are more effective for ion collection (because the ion beam tends to diverge). It is found that a detector with rings of 2.54 cm i.d. provides a good compromise between effective image charge formation and ion collection, as this detector produces higher signal intensity for protonated insulin ion than those made of rings of 1.27 cm i.d. and 5.08 cm i.d. Because the output signal (Pout) is directly proportional to the feedback resistance, Rf, increasing Rf is very effective to increase signal amplitude. However, a larger Rf causes broader peaks and thus degrades the resolution of the detector due to a larger time constant in the detection circuit. A compromise must be made between resolution and sensitivity. An Rf of 1 MΩ is found to provide satisfactory results in both categories.

Linear Ion Trap:

A linear ion trap (LIT) was created by applying timed stopping potentials on the entrance and exit lenses of a RF-only quadrupole. In the linear ion trap, ions are trapped in the radial direction by the RF quadrupole field. The axial direction trapping is accomplished by the blocking potentials at the entrance and exit lenses. In the presence of buffer gas, the z direction translational energy of an ion is determined by the energy dampening effects of collisions with the gas. A sufficient number of collisions will result in an ion whose translational energy in the z direction is determined by the thermal motion of the background gas.

Figure 10:
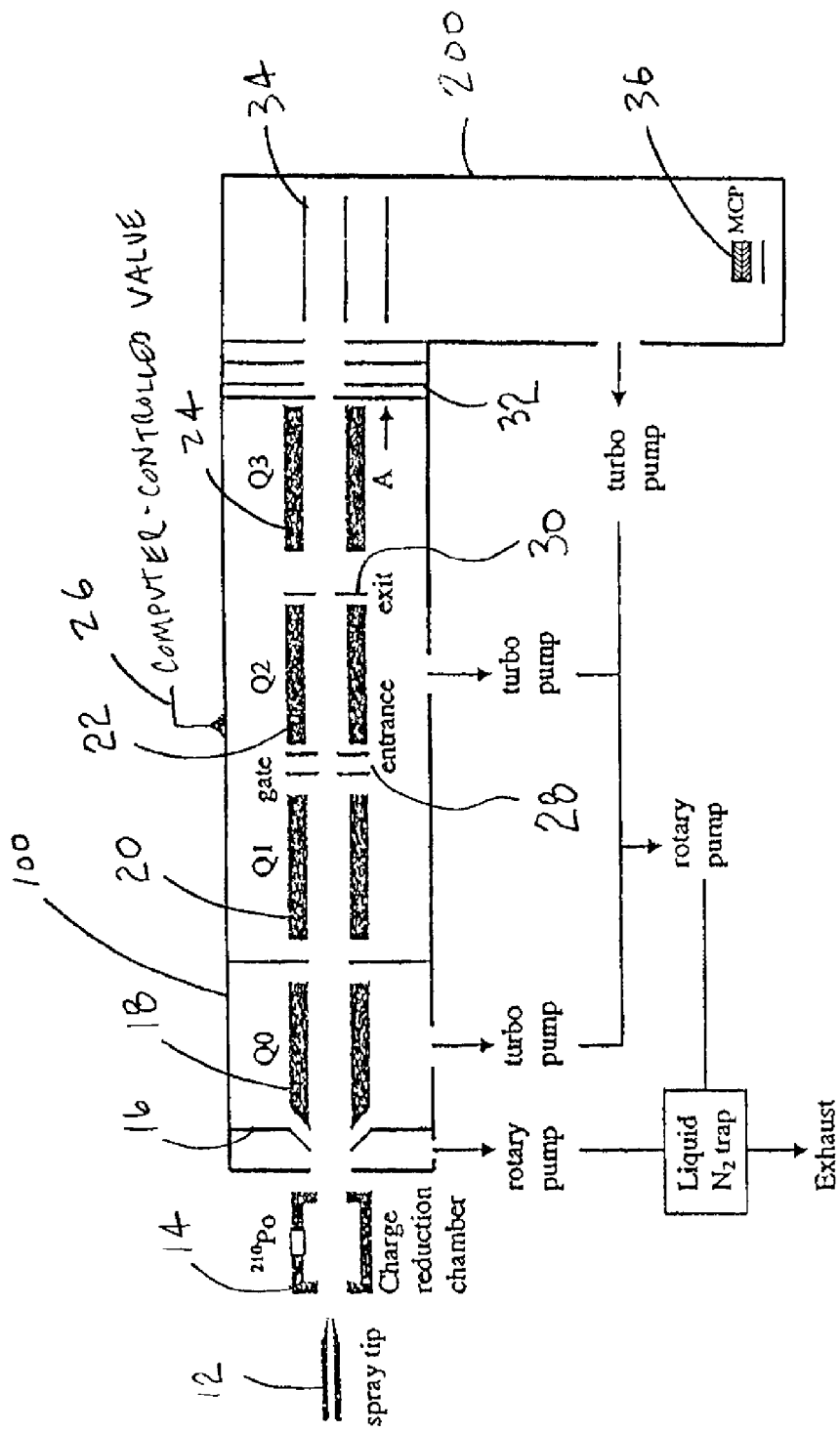
FIG. 10 is a schematic diagram of a mass spectrometer according to the present invention.

The Q/LIT/Q mass spectrometer of the present invention is shown schematically in FIG. 10. In the working embodiment of the device, the third quadrupole, q2, is 15.4 cm long and has a field radius of 6 mm. Each rod in q2 is made out of several parallel wires which together form a cylindrical surface 8 mm in radius. This construction of q2 allows the background buffer gas to traverse the quadrupole without obstructions, while confining ions inside the q2. The DC offsets of the quadrupoles are individually set with typical values of q0=30 V, Q1=20 V, q2=25 V, and Q3=20 V. The initial kinetic energy of an ion as it enters q2 is determined by the DC offset difference between q0 and q2 (5 eV for a singly charged ion at a typical setting). At these physical dimensions and settings, it takes 70 μs for a 5 eV ion of m/z 200 to travel through q2.

Figure 11:
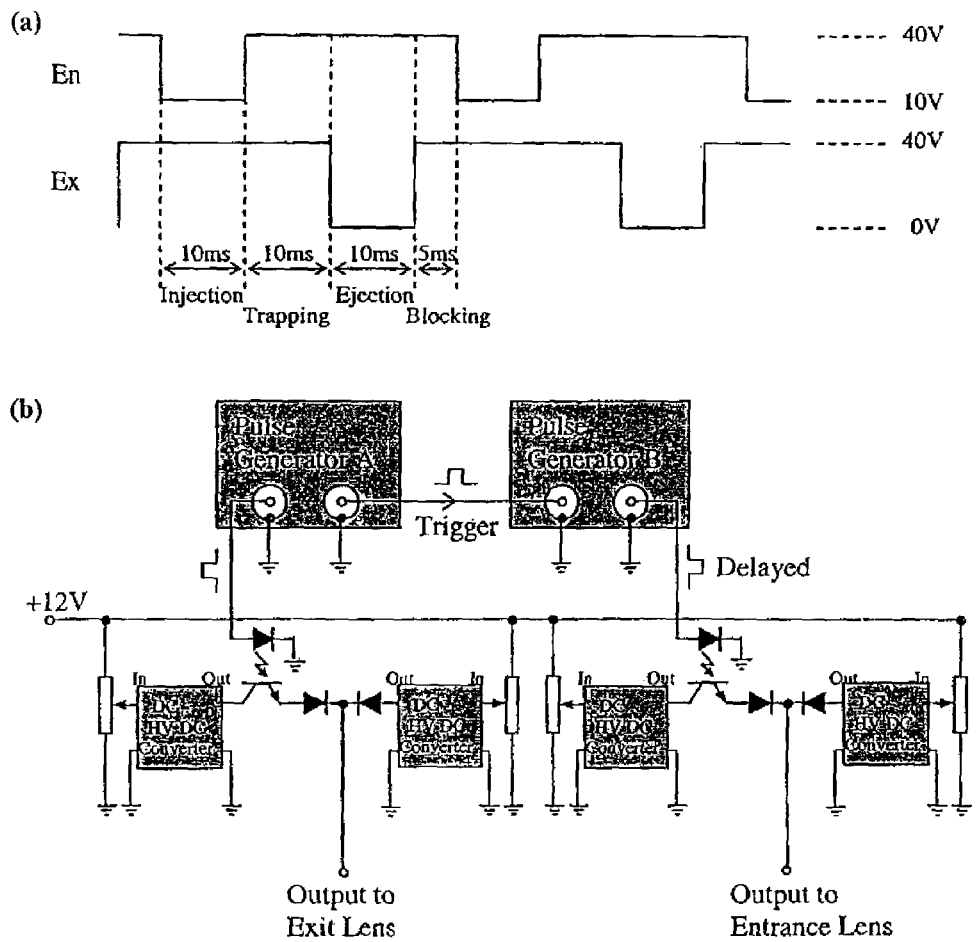
FIG. 11 is a schematic diagram depicting the potential and timing parameters for a typical 35 ms trapping cycle.

The voltages on the entrance and exit lenses are controlled by a circuit as illustrated in FIG. 11B. In normal QqQ MS mode, the entrance and exit lenses are held at 10 V and 0 V, respectively. The timing parameters of a trapping cycle are controlled by two pulse generators and is shown schematically in FIG. 11A. Of the two pulse generators, one (pulse generator A in FIG. 11B) provides the master clock and triggers a delayed pulse sequence from the second pulse generator (pulse generator B in FIG. 11B). The first phase of a trapping cycle is ion injection. The potential on the exit lens is raised to a higher value (40 V) as controlled by pulse generator A. After an injection period of 10 ms to 100 ms, as controlled by the delay time on pulse generator B, the potential on the entrance lens is toggled to the same level as that on the exit lens (40 V) to prevent ions from both entering the trap and escaping from the trap in the z direction. This starts the trapping period, typically 10 ms to 1000 ms. Ion ejection is achieved by lowering the voltage on the exit lens to 0 V, while keeping the voltage on the entrance lens high (40 V) for a period of 10 ms to 100 ms. In practice, there is usually a blocking period (0 to 5 ms) prior to the next injection step in which voltages on both entrance and exit lenses are held high. This is to prevent precursor ions from traversing the LIT without being trapped. A trapping cycle is completed after the blocking period. An important feature of this design for the driving electronics is its flexibility in different operation modes. The Q/LIT/Q mode can be switched to the normal QqQ mode simply by turning off the pulse generators.

Ions are trapped in the radial direction by the RF quadrupole field. The axial direction trapping is accomplished by applying blocking potentials at the entrance and exit aperture. In the presence of buffer gas, protein ions injected into ion trap lose their translational energy in the axial direction upon collisions with a neutral target and thus are trapped inside the potential well. The trapping process can be simulated using SIMION 3D-brand software (version 7.0), distributed by Scientific Instrument Services, Ringoes, N.J.

The physical dimensions of the preferred ion trap are: l=154 mm, r=8 mm, $r_0$=6 mm, where l is the length, r is the radius of the cylinder rod and $r_0$ is the inscribed radius. The RF potential applied to the quadrupole rods is defined by:

$$V = V_{rf} \cos(2\pi f t) \quad (4)$$

where $V_{rf}$ is the RF amplitude, f is the RF frequency in Hz, and t is the flight time of the ion. The rods are coupled so there is a phase difference of π between the values of $V_{rf}$ applied to the two pairs of opposite electrodes. One important feature is the use of a 3D hard sphere collision model for simulating the ion-buffer gas interactions.

The collision frequency for an ion is calculated using the following equation:

$$Z = \sigma \overline{V}_{rel} N \quad (5)$$

where σ is the collision cross section, $V_{rel}$ is the averaged relative velocity between the ion and the buffer gas, and N is the gas number density.

Because the buffer gas molecules may move toward the ion or leave the ion along the direction of the relative velocity before they collide, statistically the ion and buffer gas approach the collision point at a 90° angle relative to each other:

$$\overline{V}_{rel} = (\overline{V}_1^2 + \overline{V}_2^2)^{1/2} \quad (6)$$

where $V_1$ and $V_2$ are the average velocities of the ion and buffer gas molecule between collisions.

Gas number density is calculated from its pressure, which can be adjusted at the beginning of each run. The collision cross section of incident ions is assumed to be 1000 Å$^2$ (singly-charged ubiquitin ion),[35, 36] and the radius and molecular weight of the buffer gas molecule is assumed to be 2 Å and 40 a.u. (argon). The lab frame velocity of buffer gas, $V_2$ is defined by:

$$\overline{V}_2 = \sqrt{\frac{8kT}{\pi m_2}} \quad (7)$$

This is the mean value for a Maxwellian distribution of velocities, where k is Boltzmann's constant, T the gas temperature, and $m_2$ the mass of one gas molecule.

The mean free path of the ion is given by:

$$\lambda = \overline{V}_1 / Z \quad (8)$$

Because the velocity of an ion changes between two collisions due to the RF driving potential, at each time step $V_1$ is calculated by dividing the path the ion has passed since the last collision ($L_p$) by the time of this period ($T_p$). $V_1$ is then used to calculate Z and λ. If $L_p$ is larger than λ, then there is a collision. If not, the current time step (δt) is added to $T_p$ and δt*$V_1$ is added to $L_p$. $V_1$ is the current velocity of the ion. This process repeats until $L_p$ is larger than λ and a collision occurs. $T_p$ and $L_p$ are then set to 0 and the above steps are repeated to determine the next collision event.

When a collision does occur, the new magnitude and direction of ion velocity is calculated and assigned to the ion.

The ratio of lab frame energy of an ion after collision ($E_{lab}'$) to that before collision ($E_{lab}$) is given by:[15]

$$\frac{E_{lab}'}{E_{lab}} = \frac{m_1^2 + m_2^2}{M^2} - \frac{m_2 E_{int}}{M E_{lab}} + \frac{2 m_1 m_2}{M^2} \left(1 - \frac{E_{int} M}{E_{lab} m_2}\right)^{1/2} \cos\theta_{cm} \quad (9)$$

where $M=m_1+m_2$, $E_{int}$ is the energy transferred to internal energy of the collision partners, and $\theta_{cm}$ is the scattering angle in the center-of-mass coordinates. For large protein ions, $E_{int}$ is approximately given by the center of mass energy $E_{CM}$. Thus, Eqn. (9) can be simplified to:

$$\frac{E'_{lab}}{E_{lab}} = \frac{m_1^2}{M^2} \qquad (10)$$

Eqn. (10) is used to calculate the magnitude of ion velocity after collision, which is given by:

$$V'_1 = \frac{m_1}{m_1+m_2} V_1 \qquad (11)$$

The direction of this new velocity vector is derived by assuming an average CM scattering angle ($\theta_{cm}$) of 90°. Ion velocity in a CM system is given by:

$$V_{cm1} = \frac{m_1}{m_1=m_2} V_{rel} \qquad (12)$$

The velocity of the center of mass in lab frame is given by:

$$V_{CM} = \sqrt{\frac{m_1^2 V_1^2 + m_2^2 V_2^2}{m_1+m_2}} \qquad (13)$$

Applying trigonometric rules gives:

$$\tan a = \frac{V_2}{V_1} \qquad (14)$$

$$\sin\beta = \frac{V_{cm1}\sin a}{V_{CM}} \qquad (15)$$

$$\sin\gamma = \frac{V_{CM}\sin(\frac{\pi}{2}-a-\beta)}{V'_1} \qquad (16)$$

and $$X = \left|\frac{\pi}{2} - \gamma - a\right| \qquad (17)$$

The angle of $\chi$ defines a cone of scattering surrounding the original velocity vector. A random point on the cone is generated to define the new azimuth and elevation angle of the post-collision ion trajectory.

The simulated trajectories for an ion having a m/z ratio of 8566 (in this case, ubiquitin, cross section ~1000 Å²) with an initial translational energy of 10 eV, shows that origins are displaced in the y direction by 1 mm. In this simulation, DC voltage on the entrance and exit apertures is 5 V and 10 V respectively. The argon gas pressure can be altered to investigate trapping efficiencies at different gas density. With a sufficient number of collisions, an ion will loss part of its initial kinetic energy and be trapped inside the potential well. Damping an ion's translational energy continues until the ion reaches its thermal equilibrium.

In a quadrupole field, a trapped ion oscillates at specific frequencies determined by its m/z ratio:[37]

$$\omega_n = (2n+\beta)\frac{\Omega}{2} \qquad (18)$$

where n is an integer, $-\infty < n < \infty$, and $\beta$ is given approximately by:

$$\beta \approx \sqrt{\left(a+\frac{q^2}{2}\right)} \qquad (19)$$

If $\beta \leq 0.4$, (where $q \leq 0.6$ in an RF-only quadrupole) then the adiabatic approximation is valid and ion motion in the quadrupole field acts as the secular motion of a charged particle moving in a harmonic "pseudopotential" well of depth shown by:

$$D=(q/8)*V_{rf} \qquad (20)$$

Each m/z thus has a unique fundamental resonant frequency:

$$\omega_0 = \frac{q}{\sqrt{8}}\Omega \qquad (21)$$

If an AC auxiliary voltage with the same frequency is applied on one set of pole pairs, the ions will absorb this energy and convert it to kinetic energy. This is how resonant excitation is accomplished. Resonant excitation can be used either to remove unwanted ions, or to increase ion kinetic energy to promote ion-molecule reaction or collision-induced dissociation. The collision frequency is increased due to the increased ion velocity and a larger amount of internal energy is stored after each collision which will be available for later reactions. When energy increases from resonant absorption are greater than D, or equivalently, the ion oscillation amplitude exceeds $r_0$, the ion will escape from the trap or collide with one of the poles. While pulsed or off-resonance irradiation is used to facilitate reactions, a continuous resonant irradiation is used to eliminate unwanted ions, e.g., protein ions at higher charge states.

Resonant excitation was modeled using the SIMION 3D-brand software. Actual resonant frequency is found to be 3% higher than the calculated value using Eqn. (21). The motion of a m/z 5000 ion upon resonant excitation shows the amplitude of excitation AC waveform is 1 V, with a frequency 6.37 kHz. If the excitation source frequency is shifted even slightly, the ion will oscillate with a periodically changing amplitude.

For example, an ion having a m/z of 5000, excited at 6.31 kHz (1% lower than its resonant frequency) has an average energy when passing the center xz plane of 0.3 eV, about one half of D, and 10 times higher than its thermal energy. This off-resonance excitation provides a simpler operation because a continuous irradiation can be used.

Before actual degradation, the molecular weight of the protein of interest is measured to determine the excitation frequency in the first degradation cycle. The excitation frequency is then adjusted (increased) accordingly as the mass of the parent ion decreases after each cycle of degradation.

Charge Reduction:

Peptide fragmentation can be suppressed by fixing the site of the charge within the ionized peptide. Because a singly-charged ion is most likely to have the proton localized to the most basic site on the ion, one approach is to conduct Edman degradation on singly-charged protein ions only. However, large protein ions usually have a very low abundance at the singly charged state. For this reason, charge reduction techniques[32-34] are used to reduce the charge state of protein ions.

A charge reduction chamber/reaction chamber 14 (see left-hand side of FIG. 10) is positioned between the ionization source 12 and the entrance of the triple quadrupole mass spectrometer 100. In the charge reduction chamber, gas molecules ($N_2$ or $CO_2$) are ionized (normally in a corona discharge or by exposure to a $^{210}Po$ α-particle source). Protein ions entering the chamber are neutralized by these ionized gas molecules. Consequently, ions leaving the charge reduction chamber have higher abundance of ions low charge states.

Singly-charged protein ions usually have a rather high m/z ratio, and band-pass filtering at such a high mass range is impractical for quadrupole mass filters. Thus, in the preferred embodiment, Q1 (20) is operated in an RF-only mode and all of the ions with m/z ratios higher than the low-mass cut-off value (LMCO) will transmit and enter the collision cell 22 (i.e., the linear ion trap). When entering the ion trap, an ion's initial kinetic energy is determined by its charge state and is offset between Q0, 18, and the ion trap. Ions at higher charge states will have lower trapping efficiencies because of their higher injection energy. If desired, complete elimination of charge states other than unity can be accomplished by resonant excitation.

Gas-Phase Edman Degradation:

Each gas-phase Edman degradation cycle includes three major steps: (i) a coupling reaction of protein ions with PITC, (ii) a cleavage reaction of FTC derivatives, and (iii) a mass measurement of AZT derivatives. See FIG. 1. Because conversion of AZT to PTH is slow compared to ion detection, and because there is no mass difference between AZT and PTH derivatives, conversion is not necessary in gas-phase degradation.

In the preferred mode of the invention, the DC voltage offsets of the quadrupoles are individually set at Q0=10 V, Q1 (20)=5 V, Q2 (22)=0 V and Q3 (24)=0 V for all sequencing steps (see FIG. 10). The argon buffer gas pressure in Q2 and Q3 is maintained at 2 mTorr.

Referring specifically to FIG. 10, ions are preferably generated by pneumatically assisted electrospray (+4 kV), although any type of ion generator 12 now known (ESI, MALDI, electron discharge, etc.) or developed in the future may be utilized. The ions pass through the charge reduction chamber 14 at +250 V. Ions at lower charge states are sampled at a nozzle/skimmer assembly 16 (+15 V) that leads to the first low pressure region of the mass spectrometer (1 to 10 Ton).

Ion Injection and Isolation:

During injection, voltage applied to the entrance 28 and exit 30 (again, see FIG. 10) is set preferably at 5 V and 10 V while the gate 29 is grounded. Initial ion kinetic energy is determined (at these settings) by the DC offset difference between Q0 and Q2,[35] which is preferably 10 V. The buffer gas pressure is maintained at 2 mTorr. At the end of the injection period, the potential on the gate and entrance aperture is toggled to 100 V and 10 V, respectively, to prevent ions from entering the trap. When necessary, parent ion isolation can be accomplished through the use of a notched broadband excitation waveform.[38] A typical broadband waveform will span frequencies from 1 kHz to 300 kHz (30 kDa to 100 Da), created by a comb of sine waves each with an amplitude of 10 V and separated by a frequency of 500 Hz. A typical notch in the broadband waveform is 1 kHz wide and is centered on the resonant frequency corresponding to the ion of interest.

Linear ion traps of different design to the one described here have been used for ion storage.[38-40] However, some important characteristics of ion traps remain unexplored. By considering equilibrium conditions between the space-charge repulsion field and the RF focusing field, charge capacity for a quadrupole 10 cm long is estimated to be ~$10^{10}$ electrons. Experiments designed to investigate the trapping efficiency and charge capacity of this linear ion trap measure the ion current entering the trap using a charge detector (a tube[41] or simply a metal plate) placed at the end of the spectrometer.

All the quadrupoles are operated at high pass mode. Current, i, is measured as a function of the flow rate at the ESI source and is used to calculate the amount of ions entering the ion trap. At the same flow rate, ions are continuously injected into the ion trap for a period of $t_1$(ms). This time is controlled by toggling the gate voltage in front of the entrance aperture. After $t_1$, ions in the trap are ejected for detection. The ratio between the charge measured and the product of $i*t_1$ yields the trapping efficiency of the ion trap. The charge capacity is evaluated by increasing $t_1$ until the total charge ejected reaches some maximum value. To investigate how well the trap can contain charges, the injection time $t_1$ is fixed while ejection is delayed for a period of $t_2$ (seconds or minutes).

Coupling Reaction:

After accumulating protein ions, gas-phase phenyl isothiocyanate (PITC) is introduced into the ion trap at pressure of 1-10 mTorr through a computer controlled valve (26 in FIG. 10). To facilitate the reaction, ions are excited by off-resonance irradiation. At the end of the coupling step, the PITC gas is pumped away in approximately 2-3 seconds.

The coupling step is studied individually by injecting protein or peptide ions into the PITC gas-filled trap. After a certain reaction period, all the ions are ejected for mass measurement to obtain the relative abundance of reactant and products.

Earlier kinetic studies[42] on condensed-phase coupling reactions between PITC and glycine show an activation energy of 17.6 kcal/mole, based on collision theory. Using glycine, the coupling reaction is very slow at room temperature. Even at 70° C., the reaction requires 100 seconds for 90% completion; while an improvement, this remains unsatisfactory for fast sequencing. Therefore, alternate Edman reagents with higher reactivities are required. Earlier studies have shown that glycine with modified PITC[34] and pentafluoroisothiocyanate[43] has increased reaction rates, but others should perform better still. Table 1 shows some candidate reagents tested.

TABLE 1

Some properties of R-PITC and rate constants of their reaction with Glycine.

| R-PITC | m.p./K | b.p./k | Vapor Pressure @ 298K/Pa$^f$ | $k_{NH2}^c$ 1·mol$^{-1}$·min$^{-1}$ |
|---|---|---|---|---|
| H | 252$^2$ | 494$^2$ | 25.9 (24.1$^g$) | 14.6 |
| 3-fluoro- | | 500$^2$ | 19.4 | |
| 4-fluoro- | 300$^{b,d}$ | 501$^b$ | 17.7 | |
| 2-chloro- | | 534$^b$ | 3.6 | |
| 3-chloro- | 318$^c$ | | | 22.2 |
| 4-chloro- | 319$^a$ | 522.5$^a$ | 4.0 | |
| 2-bromo- | 293$^d$ | 530$^d$ | 4.4 | |
| 3-bromo- | | 529$^b$ | 4.4 | |

TABLE 1-continued

Some properties of R-PITC and rate constants of their reaction with Glycine.

| R-PITC | m.p./K | b.p./k | Vapor Pressure @ 298K/Pa[f] | $k_{NH2}$[c] $1 \cdot mol^{-1} \cdot min^{-1}$ |
|---|---|---|---|---|
| 4-bromo- | 333[c] | | | 21.1 |
| 4-nitro- | 384[b] | 590[e] | 0.028 | 163 |
| Penta-fluoro- | | 508.5[c] | 12.8 | |

[a]CRC handbook of chemistry and physics, 70th Edition
[b]Acros Organics, Catalog of organics and fine chemicals, Fisher Scientific, 2002
[c]Ref.[66]
[d]Lancaster Catalog, 2000
[e]Estimated using group contribution values from Ref.[36]
[f]Unless otherwise notified, vapor pressures were calculated using an empirical formula $$\ln[p(atm)] = -(4.4 + \ln T_b)\left[1.803\left(\frac{T_b}{T} - 1\right) - 0.8031\ln\left(\frac{T_b}{T}\right)\right] - 6.8\left(\frac{T_m}{T} - 1\right)$$

[g]NIST chemistry webbook

In search of a new Edman reagent, ab initio calculations are used as a selection guide. This calculation was performed at the B3LYP level of correlation theory using a standard 6-31G* basis set (results not shown). All optimized structures were subject to vibrational frequency analysis with the same basis set to ensure they corresponded to minima on the potential energy surface. Energies were corrected for zero-point vibrations scaled by 0.8929 and transition states were located using keyword QST2 or QST3. Finally, IRC calculations followed by optimization and frequency calculations were performed to confirm reaction pathways.

Cleavage:

As PITC is pumped away, trifluoroacetic acid is delivered into the ion trap to cleave the peptide bond at the N terminus of the PTC derivative. TFA is a strong volatile acid which has been used successfully in gas-phase sequencers. The TFA gas pressure is maintained at 1 to 10 mTorr, and off-resonance excitation is applied. PTC derivatives are prepared in solution first, then studies similar to that on coupling reaction can be conducted.

In an alternate approach, the buffer gas pressure is adjusted without introducing TFA. Cleavage is achieved by collision-induced dissociation. PTC derivatives have a specific fragmentation pattern that breaks only the N-terminus peptide bond.[44-46] The proposed mechanism for fragmentation of PTC derivatives is similar to that of a protein ion (see FIG. 5). Because the proton is localized after charge reduction, the energy requirement for cleavage of the N-terminal peptide bond in PTC derivatives is also enhanced. This can be accounted for by using a longer reaction time (ions are trapped instead of passing through) and excitation. Given the fact that modified $b_1$ ions (and its counter part $y_{n-1}$ ions) were formed almost exclusively when a mobile proton is available, it is possible to allow dissociation of PTC derivatives while minimizing nonspecific fragmentation of protein ions.

If acid cleavage involves proton transfer from TFA to oxygen, then the difference in energy requirements between these two approaches can be estimated by the difference of $G_{acid}$ of TFA and gas-phase basicity (GB) of arginine, the most basic amino acid. These two quantities are defined by the free energy change in the following reactions:

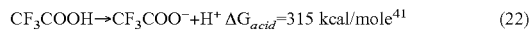

$CF_3COOH \rightarrow CF_3COO^- + H^+$  $\Delta G_{acid}$=315 kcal/mole[41]  (22)

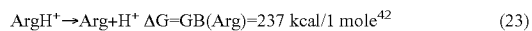

$ArgH^+ \rightarrow Arg + H^+$  $\Delta G$=GB(Arg)=237 kcal/1 mole[42]  (23)

It can be seen from Eqn. (22) and (23) that mobilizing protons from a basic side chain requires a lower energy input. However, complete acidic dissociation might not be necessary in gas-phase acid cleavage. For instance, formation of an intermediate with a hydrogen bridge structure might be sufficient to initiate cleavage.

Reionization:

As the sequencing continues, at some point the basic residue is cleaved, resulting in a doubly-charged modified $b_1$ ion and a neutral fragment. To maintain the neutral fragments for further sequencing, a reionization reagent, $MeOH_2^+$, is injected into the ion trap by setting Q1 accordingly at the beginning of each cleavage step. Proton transfer from $MeOH_2^+$ to peptide is energy-favored because MeOH has a lower proton affinity as compared to the peptide.[47, 48] Furthermore, proton transfer has a negligible energy barrier, so the reionization rate is solely determined by the collision frequency. For example, in the unimolecular dissociation of an excited precursor ion, there is no kinetic energy release so that the fragment ion and neutral fragment move apart in the center of mass coordinate system with minimal kinetic energy. In the lab frame, the fragment ion moves with the same speed as the precursor ion. Under off-resonance excitation, this speed is approximately 0.1 mm/μsec for a m/z 5000 precursor ion. The collision frequency of a neutral fragment with $MeOH_2^+$ must be higher than $10^5$ (equivalent to a mean free path of 1 mm) to keep it inside the ion trap. The required number density of $MeOH_2^+$ can be calculated from Eqn. (5). Assuming a collision cross section of 1000 Å$^2$, the minimum number density of $MeOH_2^+$ required is $10^{10}$ m$^{-3}$. Given a linear ion trap volume of approximately $10^{-5}$ m$^3$, the total number of $MeOH_2^+$ required is $10^5$. This value is readily achieved because the charge capacity of a linear ion trap of the stated volume is approximately $10^{10}$ e.

Figure 12:
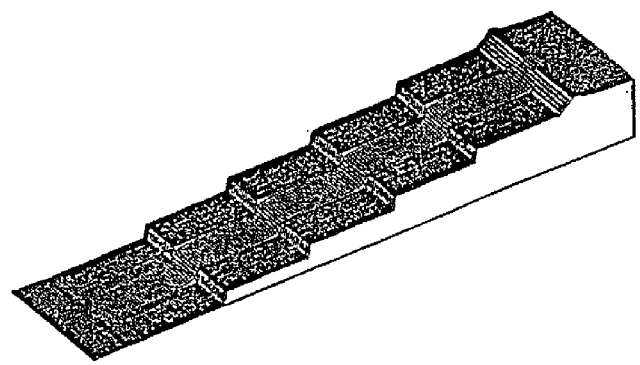
FIG. 12 is a three-dimensional, cross-section through the axial yz plane of a segmented rod quadrupole ion trap.

Moreover, it is likely that the proton will be transferred to the most basic residue of the neutral fragment, either directly from $MeOH_2^+$ or through an intramolecular bridge.[49] Ion-ion repulsion prevents any additional protonation to the already charged peptide. After reionization, singly-charged ions are formed with their proton localized at some basic site Ion Ejection:

Simply applying DC voltage on the entrance and exit apertures for axial ejection of ions is very inefficient. No potential gradient exists for the majority of the length of the cell. Therefore, to create an effective axial acceleration field, the original quadrupole collision cell is replaced by a segmented quadrupole cell.[36, 50] The segmented cell was modeled using the SIMION 3-D-brand software (see FIG. 12). This cell contains five segments. As can be seen in FIG. 12, the voltage progressively decreases from the entrance to the exit of the trap. In the preferred embodiment, each segment is 30 mm in length and has an inter-segment separation of 1 mm. Each segment is supplied with the same RF voltage. In practice, one DC supply is used to provide an offset to segment 1, and a second floating DC supply connected across a voltage divider provides a constant electric field along the axis. This arrangement is shown schematically in FIG. 12, which is a cross-section view through the axial yz plane of the segmented rod. As shown in the figure a DC voltage of 5 V is applied to the entrance aperture and the exit is at ground. During all other sequencing stages, the offset between segments is set at 0 V. During ejection a stepped field is formed inside the ion trap by applying a proper DC offset that steadily decreases going from the entrance to the exit of the trap (thereby accelerating the ions out of the trap).

Figure 13:
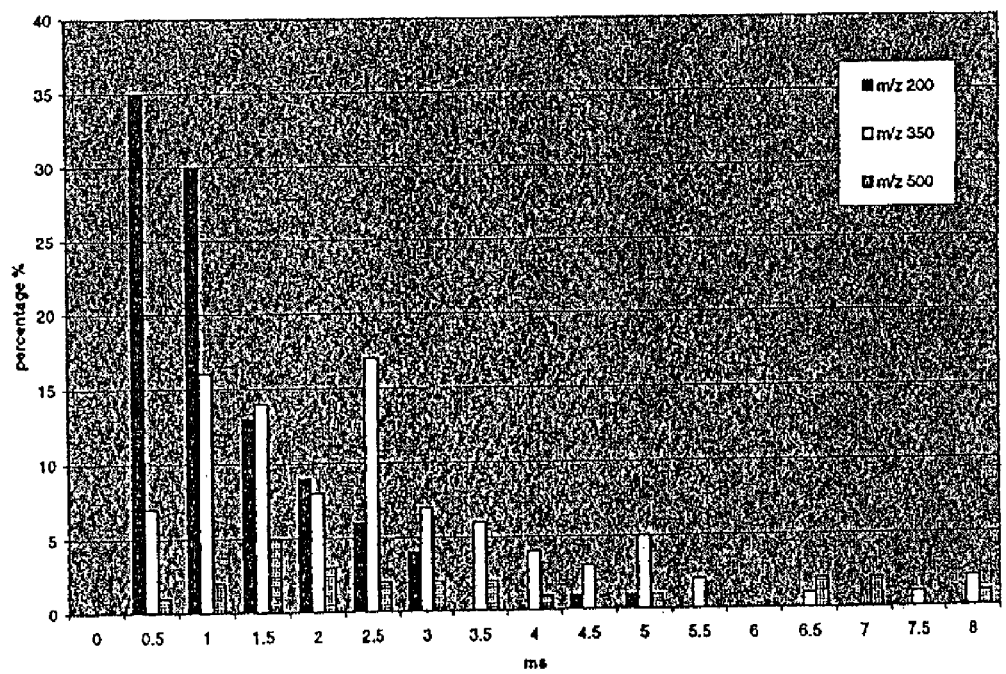
FIG. 13 is a histogram depicting the ejection time distribution for m/z 200, 350, and 500 ions. The ejection time starts at the end of a 2 ms delay.

Ideally, only modified $b_1$ ions would be ejected and all $y_{n-1}$ ions would be retained in the trap. For this purpose, an AC potential is added to the DC offset at the exit aperture. While lighter ions can escape the trap during a negative swing of the AC voltage, slower moving heavier ions cannot. Computer modeling simulations indicate that this AC voltage optimizes the ejection of small ions (m/z 100 to 350). Preferably, the buffer gas pressure is maintained at 2 mTorr, the DC voltage at the entrance aperture is maintained at 10 V, the DC offset at each segment is set at 8 V, and the voltage on the exit aperture is maintained at 10 V for 2 ms before an AC potential of 5 V (20 kHz) is applied and the DC offset is lowered to 2 V. The simulated distribution of ejection times for m/z 200 ions (100 $Å^2$), m/z 350 ions (175 $Å^2$), and m/z 500 ions (250 $Å^2$) are shown graphically in FIG. 13. At the beginning of the simulation, 100 ions were located evenly along the quadrupole axis with no initial kinetic energy. Similar simulation on m/z 1000 ions (400 $Å^2$) showed that there is no ejection up to 8 ms. The excess $MeOH_2^+$ ions are completely ejected and eliminated in Q3 (see FIG. 10), where LMCO is 100.

Detection:

As modified $b_1$ ions are ejected from the reaction cell, Q3 can be scanned at a certain rate (~5500 u/s) in a mass-to-charge range of from about 100 to about 350. A portion of the product ion passes through Q3 and is detected by an ion detector, such as a microchannel plate detector (MCP, reference number 36 in FIG. 10). A drawback of this detection scheme is the loss of sensitivity because the MCP only registers a small portion (in this case only 1/250) of product ions. Another problem is that a quadrupole mass filter requires a continuous ion source. Ions ejected from a linear ion trap do not form a uniform and continuous stream. This leads to mass-dependent detection efficiency. However, improved sensitivity can be achieved by coupling an orthogonal acceleration time-of-flight mass spectrometer 200 to the triple quadrupole system, as shown in FIG. 10.[49]

The TOF chamber 200 is coupled to the quadrupole Q3 via an aperture ("A" in FIG. 10) and focusing lenses 32. The aperture serves as the exit of the Q3 quadrupole and the differential pumping aperture between the quadrupole and TOF chambers. The TOF source region has the same DC offset as Q3, so the axial ion energy in the TOF source remains small.

It is preferable to operate Q3 at relatively high pressure. The benefit from the resultant collisional cooling effect is three-fold. First, it damps the translational energy of the ions, thereby creating a slower ion beam. This leads to higher duty cycle because duty cycle is defined as the ratio of the source filling time to the time between the acceleration pulses. Second, a slower ion beam gives a higher ion density to each pulse accelerated into the flight tube, thus enhancing sensitivity. Third, collision cooling creates a highly-collimated ion beam with small spatial and energy spread in the radial direction, which improves resolution in the TOF MS.

Referring to FIG. 10, product ions ejected from the ion trap are focused on the axis in Q3 and enter the source region of the TOF chamber. High voltage pulses (+5 kV, 30-100 μs) are applied to an acceleration grid 34. The pulses are longer in duration than the flight time of a m/z 500 ion. The signal from MCP is digitized, and the peak value used to calculate the mass of residue $y_{n-1}$ ion. This mass is subsequently used to calculate the oscillating frequency applied in the off-resonance excitation of the next cycle. These calculations are done automatically after each cycle and sent to a programmable AC waveform generator.

Post-Ionization, Pre-Mass Analysis, Gas-Phase Reaction:

In another approach, rather than performing the degradation reaction within an ion trap, the degradation reaction takes place immediately after the ionization of the protein or polypeptide reactant, and immediately prior to introducing the product ions into a mass analyzer. Thus, for example, immediately after ionization at the spray tip 12 (see FIG. 10), the ions pass into reaction chamber 14. The degradation reaction then takes place within chamber 14, and the product ions are passed into the mass analyzer 100, where the m/z of the first ion product, or the polypeptide or protein fragment ion, or both, is determined. In this approach, q2 in FIG. 10 is operated as a regular quadrupole (either as a mass-scanning quadrupole or in rf-only mode), rather than as an ion trap.

Figure 14:
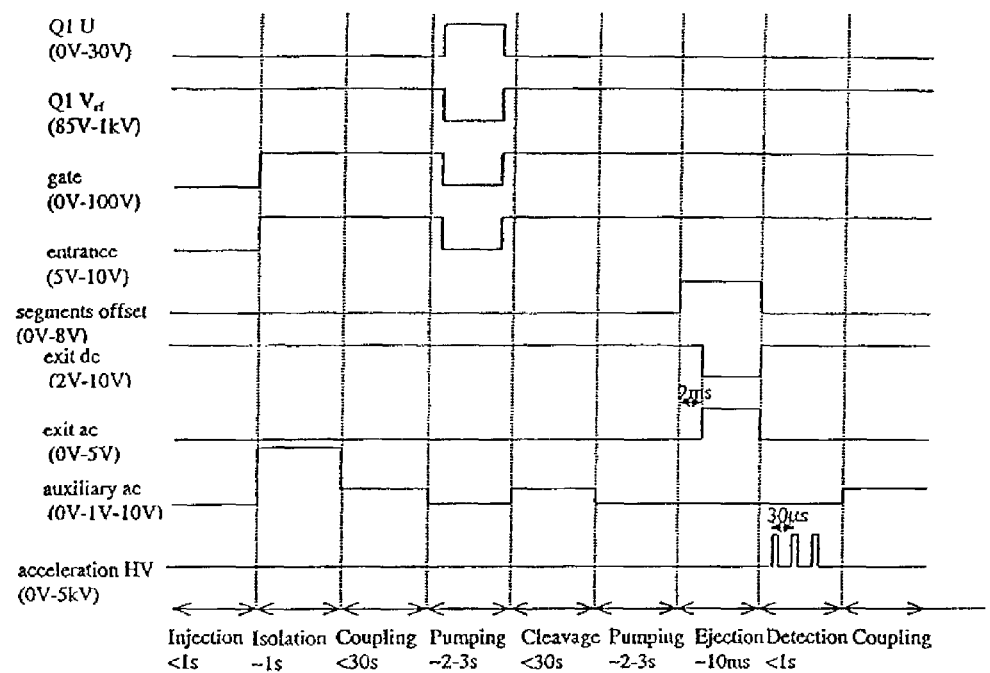
FIG. 14 is a graph depicting the timing sequence for gas-phase Edman degradation experiments within an ion trap as described herein. The voltage values in parentheses are the preferred low voltage and high voltage toggle points on each element.

Timing Sequence:

A general timing sequence for degradation experiments is shown in FIG. 14. In the preferred embodiment, Q2 and Q3 are operated in RF-only mode with $V_{rf}$ of 1 kV and an RF frequency of 3.1 MHz and 1 MHz respectively. Q0 is also operated in RF-only mode, but with $V_{rf}$ of 100 V and an RF frequency of 1 MHz to transmit $MeOH_2^+$. Q1 is switched between two operation modes: a band pass at m/z 33 during pumping interval 1 and a high pass at all other times. The frequency of the tickling voltage (for off-resonance excitation) is adjusted between cycles and between the coupling and cleavage steps in each cycle.

EXAMPLES

The following Examples are included to provide a more complete description of the invention disclosed and claimed herein. The Examples do not limit the scope of the invention in any fashion.

Materials:

All reagents, amino acids and peptides, except the TLLELAR polypeptide (SEQ. ID. NO: 1), were purchased from Sigma Chemical Co. (St. Louis, Mo.) and used without further purification. TLLELAR (SEQ. ID. NO: 1) was synthesized by the Peptide Synthesis Facility in the Biotechnology Center at the University of Wisconsin-Madison.

Condensed-phase synthesis of N-terminal methylthiocarbamoyl (MTC) derivatives:

The MTC derivatives of peptides were prepared by mixing 200 μl peptide solution (5 mM in water), 400 μl pyridine, 1 μl triethylamine, and 10 μl methylisothiocyanate (melted by warming at 50° C.) in a 1.5 ml polypropylene tube.[51, 52] The sample was incubated at 50° C. for 30 minutes, then dried in a rotary evaporator. To remove any remaining traces of volatile substances, 1 ml ethyl acetate was added to the tube. After vortexing for 10 seconds, the ethyl acetate was removed in the rotary evaporator, leaving the dry coupled peptide in the tube. The product was dissolved in 1:1 water/acetonitrile (500 μl) containing 1% acetic acid.

Instrumentation:

The work presented here was performed on an extensively modified commercial triple quadrupole mass spectrometer (API III, Perkin-Elmer Sciex Instruments, Wellesley, Mass.). To extend the gas-phase ion-molecule reaction time, the quadrupole collision cell (q2) was modified into a Linear Ion Trap (LIT) as described earlier. The DC offsets of the quadrupoles were individually set at Q0=30V, Q1=20V, q2=25V, and Q3=20V. A relatively large voltage (170 V) between the orifice and Q0 was used to reduce solvent adduction.[53] A typical collisional energy is 5 eV for singly-charged ions, as determined by the voltage difference between q0 and q2.[54] The timing parameters used in trapping cycles were: 10 ms for ion injection, 10 ms for ion trapping, and 10 ms for ion ejection.

MITC was used as the gas-phase Edman reagent and argon gas was used as the collision gas in the study of gas-phase cleavage reactions. A three-way valve was added to the background gas inlet line, which allowed introduction of MITC and argon gas alternatively. The MITC reagent was kept in its liquid form by maintaining the container at 50° C.

The instrument had a positive pressure ESI source, which comprises a long fused-silica polyimide-coated capillary (150 μm od; 25 μm id). The inlet of the capillary was immersed in analyte solution contained in a 0.5 ml polypropylene tube. A positive pressure of 10 p.s.i. was applied to the sample container. The solution was maintained at a potential of +4,500 V for positive ion mode and −4,500 V for negative ion mode through a platinum electrode immersed in the sample. The spray was stabilized with a sheath gas of $N_2$ (0.6 L/min) fed through a stainless steel tube (1.5 mm id) concentric with the silica capillary. The spray end of the capillary was positioned 1.5 cm away from the ion-sampling nozzle of the mass spectrometer.

Gas-Phase Coupling Reaction:

Amino acid and peptide ions generated by ESI were mass selected by Q1 and allowed to react with MITC gas in the LIT. The mass-to-charge ratios (m/z) of the product ions were measured by scanning the Q3 as ions were ejected from the trap. The product ion spectra of $G_n$ (where G=glycine residue and n=1 to 4) show four general types of ions were present in the spectra: (i) a protonated peptide ion. $[M+H]^+$; (ii) CID fragment ions from non-reactive collisions with the MITC gas; (iii) a coupling product ion, $[M4-H+MITC]^+$ and (iv) byproduct ions, whose mass corresponds to a loss of $CH_2$, $[A+H]^+$, or a loss of $CH_3NH_2$, $[B+H]^+$, by the coupling product ion (data not shown). It is evident from these spectra that, under the experimental conditions used, G and $G_2$ both form abundant coupling product ions while $G_3$ and $G_4$ (SEQ. ID. NO: 2) are much less reactive to MITC.

To probe the mechanism for the formation of the coupling product ion, a series of reactions were carried out. First, a variety of amino acid and peptide ions were allowed to react with MITC gas (see Table 2). A general trend emerges: the yield of the $[M+H+MITC]^+$ coupling product ion decreases as the proton affinity of the amino acids or peptides increases. Note that peptides containing arginine, which has high proton affinities relative to MITC, yield little to no $[M+H+MITC]^+$ ions. This suggests that the reaction mechanism requires a proton transfer step.

TABLE 2

Gas phase ion-molecule reactions of amino acids and peptides with MITC.

| Amino Acids and Peptides | $PA^a$ (kcal/mol) | Relative abundance (%) | |
|---|---|---|---|
| | | $[M + H]^+$ | $[M + H + MITC]^+$ |
| G | $210.5^b$ | 100 | 45 |
| A | $214.2^b$ | 100 | 85 |
| D | $216.4^b$ | 43 | 100 |
| G2 | $223.6^c$ | 90 | 100 |
| G3 | $227.2^c$ | 100 | 4 |
| G4 | $233.3^c$ | 100 | 2 |
| GLA | ND | 100 | 0.4 |
| R | $244.8^b$ | 100 | 0.3 |
| MRFA | ND | 100 | 0 |
| TLLELAR | ND | 100 | 0 |

$^a$Proton affinity (PA) of MITC (193.0 kcal/mol) taken from Karpas, Z. et al. J. Phys. Chem. 1985, 89, 5274-5278; ND = no data available.
$^b$Proton affinity of amino acids taken from Harrison, A. G. Mass Spectrom. Rev. 1997, 16, 201-217.
$^c$Proton affinity of peptides taken from Zhang, K. et al. J. Am. Chem. Soc., 1993, 115, 10812-10822.

Figure 15A:
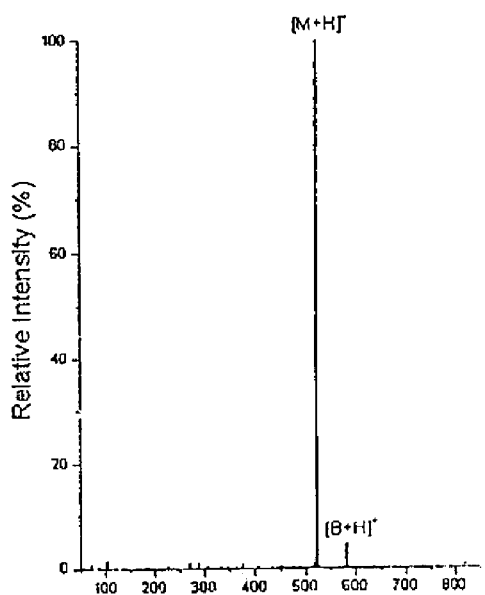
FIGS. 15A, 15B, 15C, and 15D are mass spectra of gas-phase ion-molecule reactions of the Edman reagent MITC with singly- and doubly-protonated forms of the polypeptides MRFA and TLLELAR.
Figure 15B:
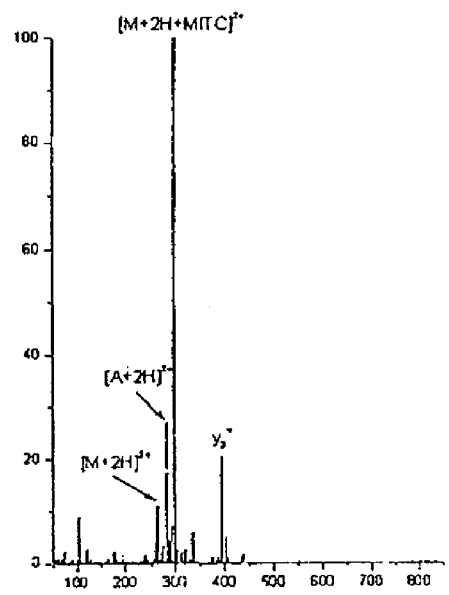
Figure 15C:
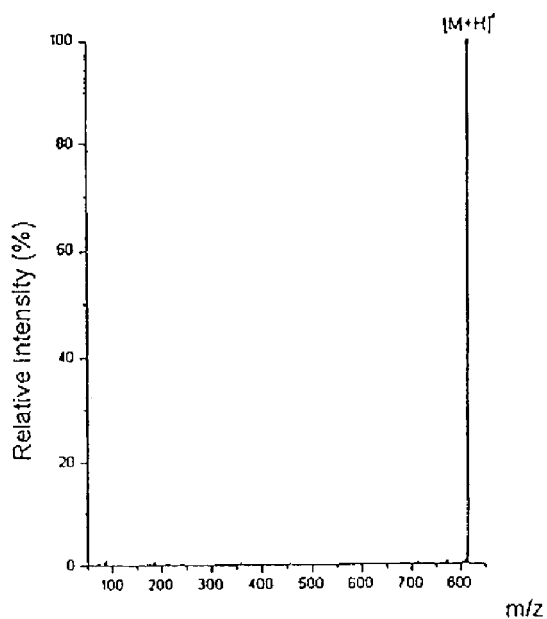
Figure 15D:
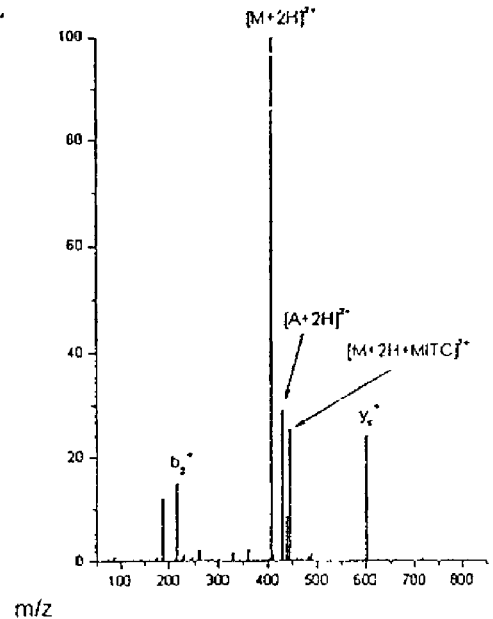

Second, both $[M+H]^+$ ion and $[M-H]^-$ ion of aspartic acid were allowed to react with MITC (data not shown). In contrast to the $[M+H]^+$ ion, the $[M-H]^-$ ion of aspartic acid forms little coupling product ion, possibly indicating a lack of a "mobile proton." Further evidence on the importance of a "mobile proton" in the coupling reaction was obtained via the reaction between MITC and doubly-protonated MRFA (SEQ. ID. NO: 3) and TLLELAR. The coupling product ion yields in both cases were relatively high (see FIGS. 15B and 15D), in marked contrast to the yields seen when using singly-protonated peptides (see FIGS. 15A and 15C). For singly-charged peptides containing a basic residue such as arginine, the proton is likely to be localized at the side chain of the basic residue.[55] Further protonation of such peptide ions provides "mobile protons," which facilitate the coupling reaction.

Figure 16:
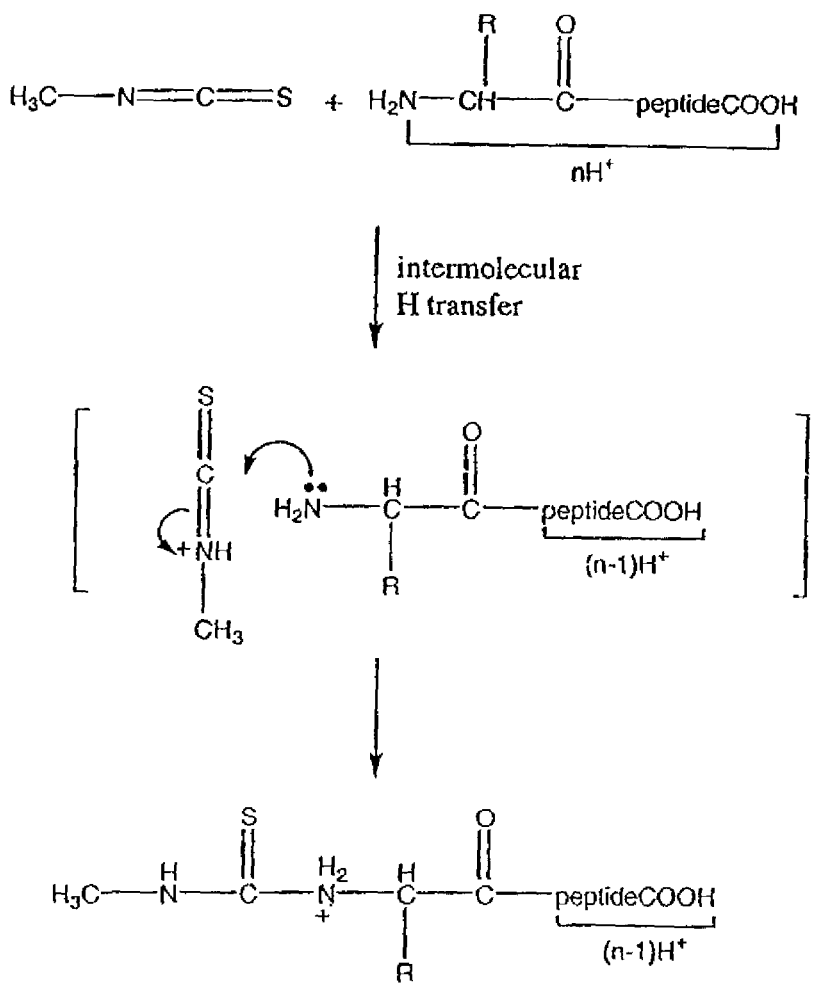
FIG. 16 depicts a reaction scheme for a possible mechanism for the gas-phase coupling reaction that involves an inter-molecular proton transfer.
Figure 17:
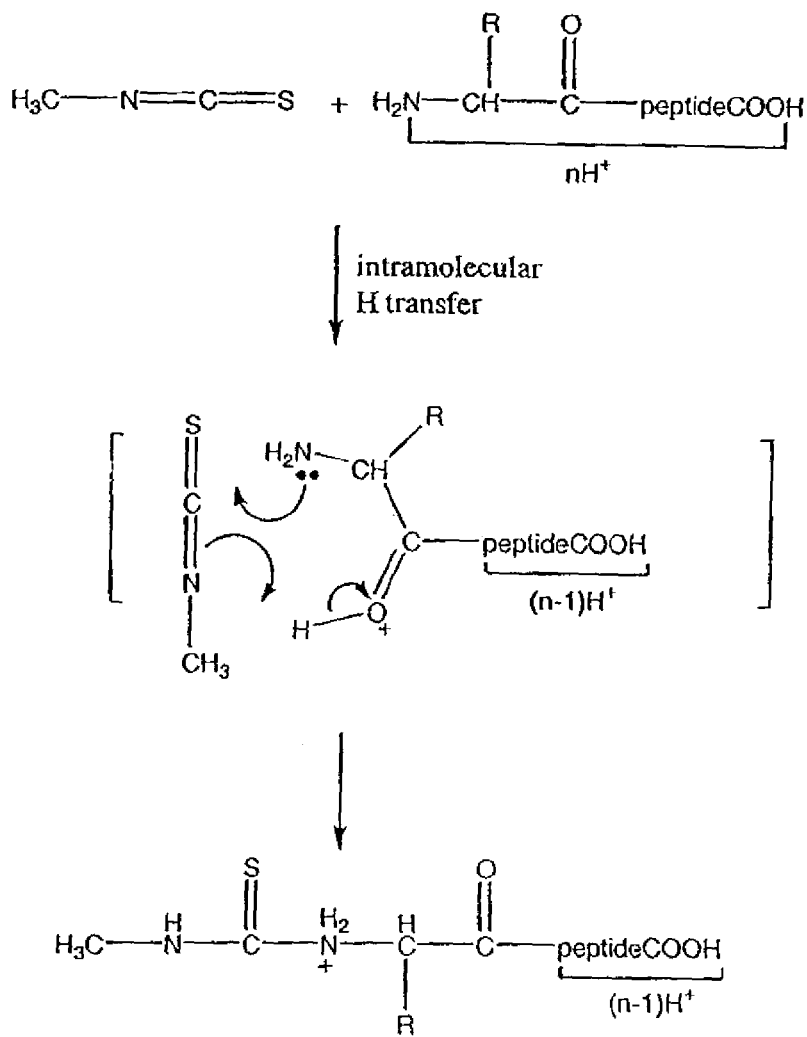
FIG. 17 depicts a reaction scheme for a possible mechanism for the gas-phase coupling reaction that involves an intra-molecular proton transfer.

Two possible reaction mechanisms may explain the experimental data. In mechanism I (see FIG. 16), a proton is transferred from the peptide ion to MITC, which initiates the nucleophilic attack of the N-terminal amino group to the thiocarbonyl group of MITC, yielding the coupling product ion. In mechanism II (see FIG. 17), the amide oxygen is protonated, followed by nucleophilic attack of the N-terminal amino group to the thiocarbonyl group of MITC. The first step in both mechanisms involves mobilization of a proton from a basic site, such as the side chain of a basic residue or the N-terminal amino group, to a less basic site, such as the nitrogen atom in MITC or the amide oxygen. Both proposed mechanisms explains why the coupling reaction is more efficient when a "mobile proton" is present.

Figure 18:
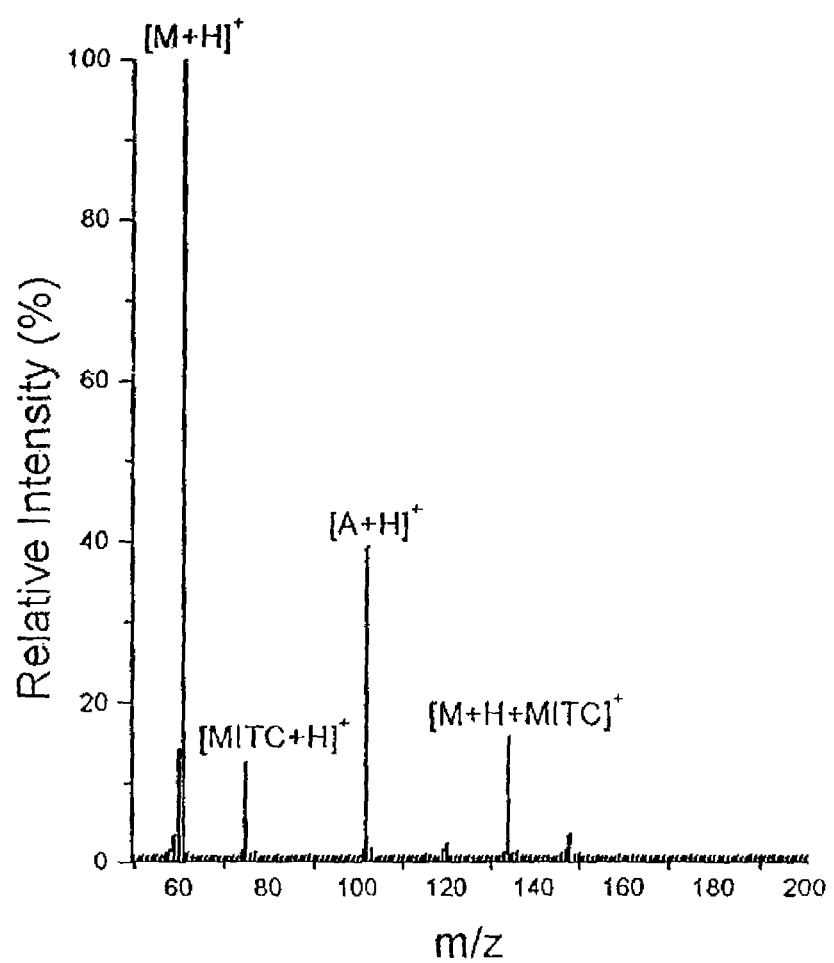
FIG. 18 is a mass spectrum of the gas-phase ion-molecule reaction of MITC with the $[M+H]^+$ ion of isopropyl amine.
Figure 19:
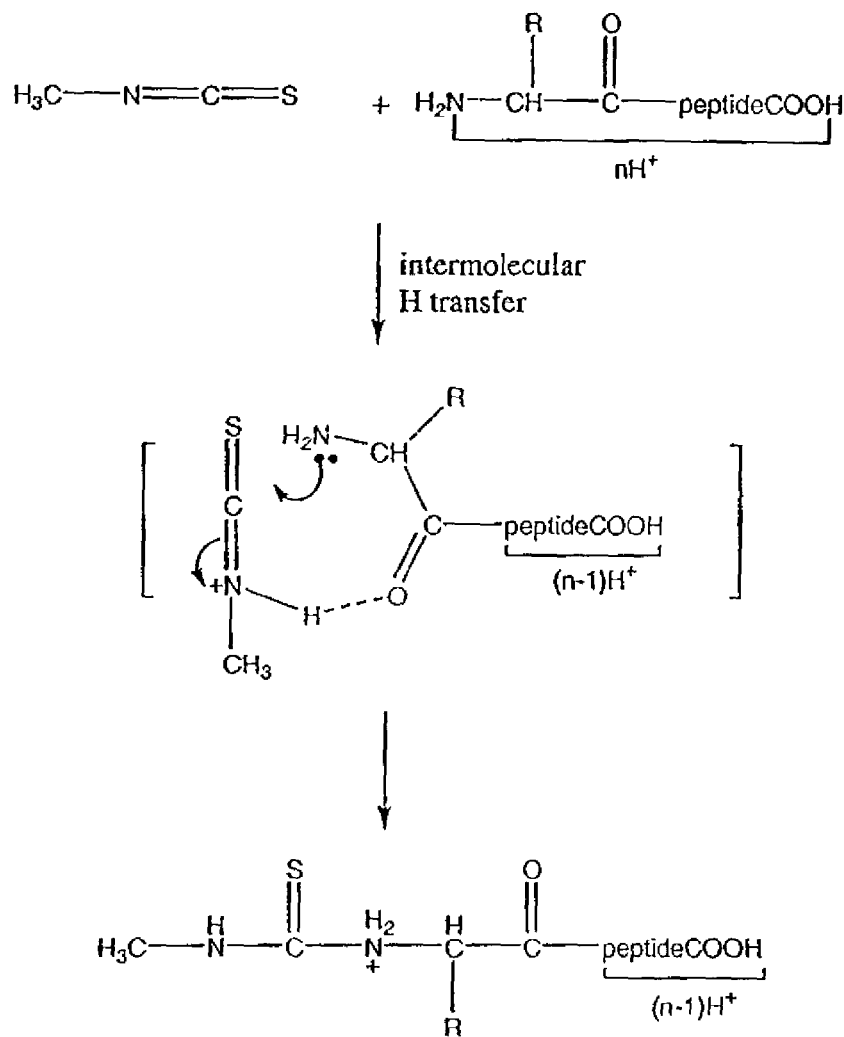
FIG. 19 depicts a reaction scheme for a possible mechanism involving an intermolecular proton transfer for the gas-phase coupling reaction between MITC and amino acids or peptides

To shed more light on the mechanism of the coupling reaction, a gas-phase reaction of MITC with isopropyl amine was performed. The resultant mass spectrum is shown in FIG. 18. Because isopropyl amine does not have a carbonyl group, the coupling product ion observed could only have been formed via mechanism I (see FIG. 16). Further, the protonated MITC ion came from an intermolecular proton transfer from the peptide ion to MITC. The proton affinity of isopropylamine[49] is 216-219 kcal mol$^{-1}$, which lies between those of G and $G_2$. Therefore, it is reasonable to assume that the intermolecular proton transfer is involved in the reaction of MITC with amino acids or peptides as well. However, the absence of a protonated MITC ion in the product ion spectra implies that the mechanism for a coupling reaction of amino acids and peptides is somewhat different (see FIG. 19). In this mechanism, after stripping the proton from the peptide ion upon collision, the MITC ion forms a complex with the peptide via a hydrogen bond which leads to the coupling product immediately. This may explain why protonated MLTC was not detected. It should be pointed out that the initial step in the coupling reaction of amino acids or peptides with MITC may be intermolecular proton transfer (mechanism III, shown in FIG. 19) or intramolecular proton transfer (mechanism II, shown in FIG. 17).

Gas-Phase Cleavage Reaction:

Low-energy CID of the peptide MTC derivatives, prepared in a solution phase coupling reaction, was performed using the modified triple quadrupole mass spectrometer. Q1 was used to select the precursor ions, which are subjected to collisions with Ar buffer gas in q2. The m/z of fragment ions were then determined by scanning Q3.

Figure 20A:
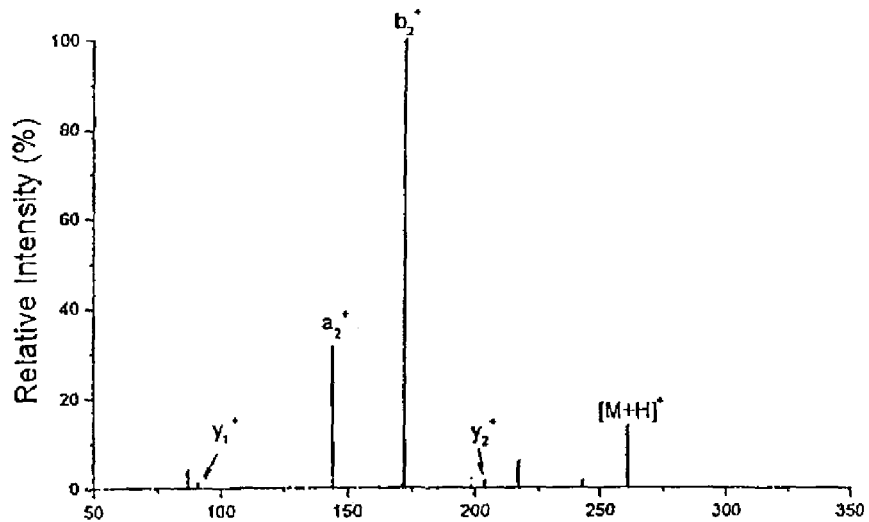
FIGS. 20A and 20B are mass spectra recorded following low-energy CID of the protonated tripeptide GLA (FIG. 20A) and the N-terminal MTC derivative of GLA (FIG. 20B).
Figure 20B:
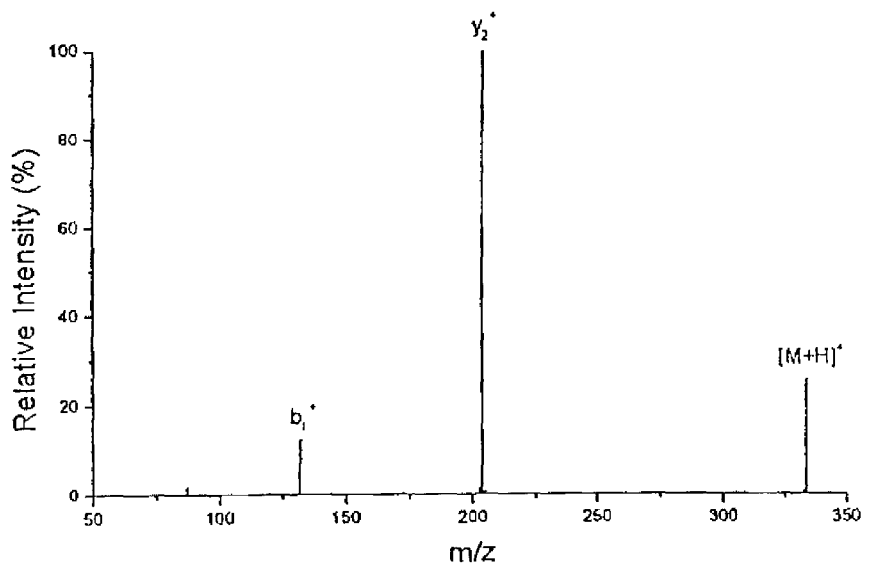

The product ion spectra recorded following low-energy collisonal activation of the $[M+H]^+$ ion of the peptide GLA and its MTC derivative are shown in FIGS. 20A and 20B, respectively. The product ion spectrum arising from CID of the $[M+H]^+$ ion of the derivatized peptide was strikingly different from that of the underivatized peptide, thus showing that these two entities are easily identifiable in the resulting mass spectra. A single fragmentation process yielded complementary singly-charged modified $b_1$ and $y_{n-1}$ product ions. During low energy collisional activation over a range of laboratory collision energies (5 to 20 eV), fragmentation was observed to occur exclusively by cleavage of the N-terminal peptide bond.

Figure 21A:
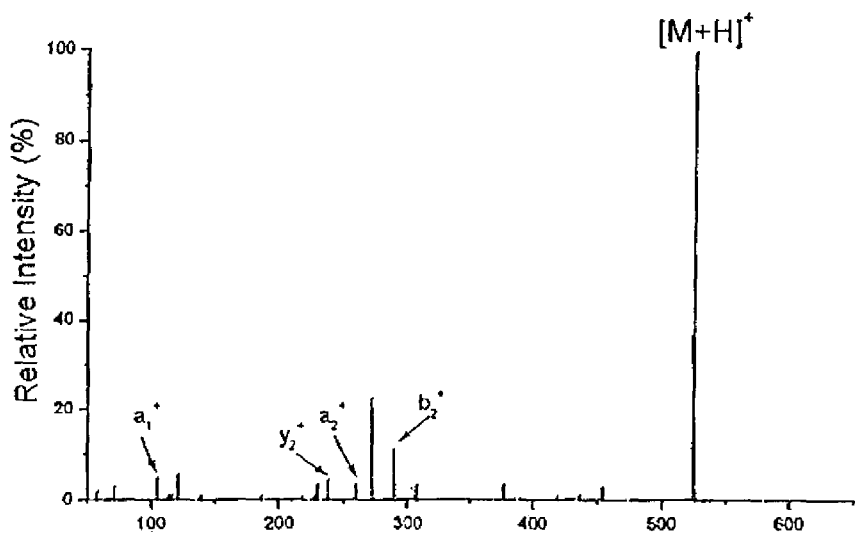
FIG. 21 are mass spectra recorded following low-energy CID of the protonated tetrapeptide MRFA (FIG. 21A) and the N-terminal MTC derivative of MRFA (FIG. 21B).
Figure 21B:
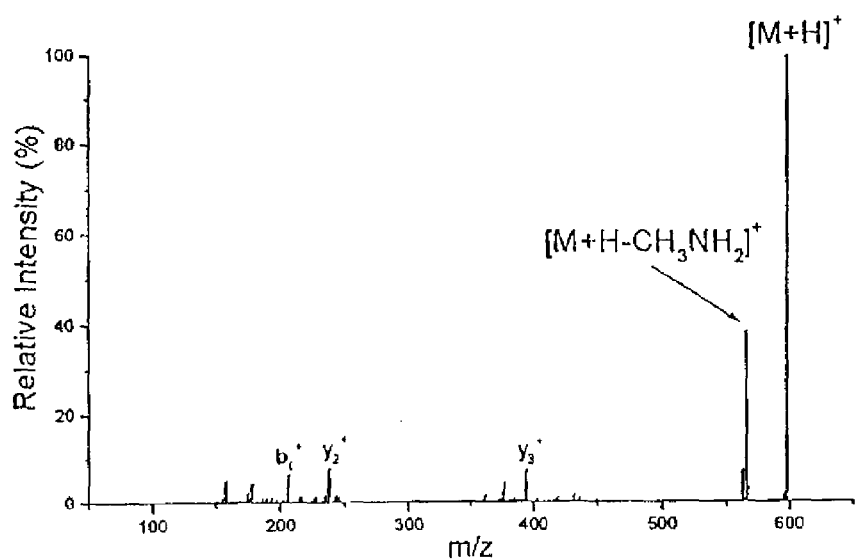

The low-energy collision product ion spectra of [M+H]$^+$ ion of the peptide MRFA and its MTC derivative under identical collision conditions are shown in FIGS. 21A and 21B, respectively. These two spectra show little fragmentation, and, more importantly, no promotion effect on modified $b_1$ ion formation was observed for the MTC derivative (see FIG. 21B). This is attributable to the preferential location of the ionizing proton on the arginine side-chain. The product ions observed (albeit in low abundance) include modified $b_1$, $y_2$ and $y_3$. Further, the high-mass fragments can be attributed to loss of $CH_3NH_2$ from the derivative group of the precursor ion. The difference between spectra implies that promotion of the formation of modified $b_1$ and its complementary y ions requires protonation of the peptide backbone. This is consistent with the observations on phenylthiocarbamoyl (PTC) related derivatives.[56-58]

Figure 22A:
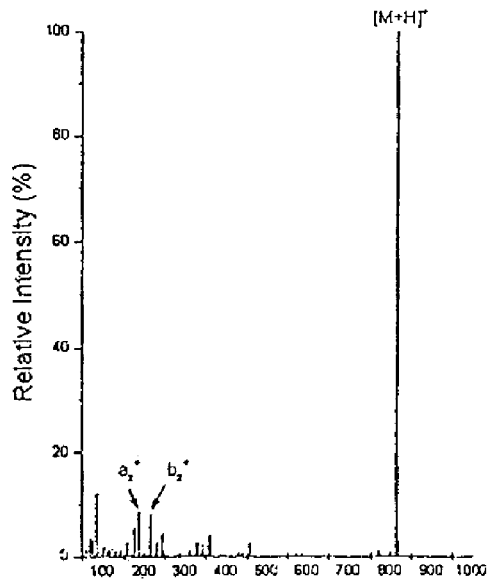
FIGS. 22A, 22B, 22C, and 22D are mass spectra recorded following low-energy CID of the singly- and doubly-charged heptamer TLLELAR (FIGS. 22A and 22B, respectively) and the N-terminal MTC derivative of singly- and doubly-charged TLLELAR (FIGS. 22C and 22D, respectively).
Figure 22B:
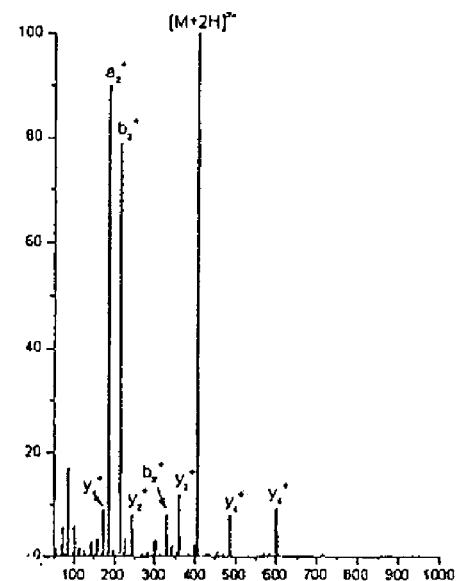
Figure 22C:
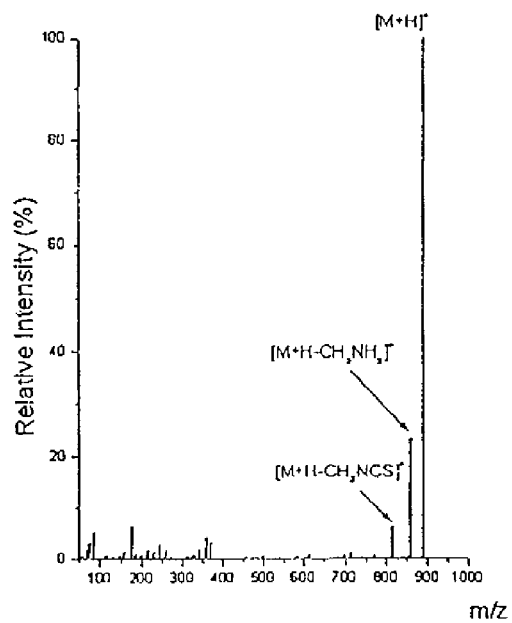
Figure 22D:
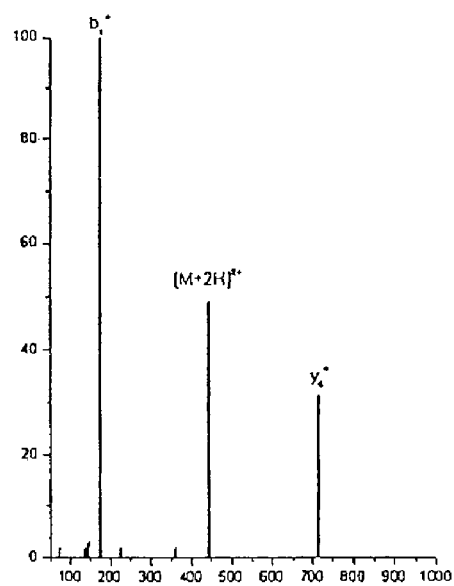

The formation of modified $b_1$ ions from [M+nH+MITC]$^+$ ions may be explained because the R group is methyl (see FIGS. 22A, 22B, 22C, and 22D). FIG. 22A is the spectrum recorded following low-energy CID of singly-charged TLLELAR; FIG. 22B is the spectrum recorded following low-energy CID of doubly-charged TLLELAR. FIGS. 22C and 22D are the spectra for the corresponding N-terminal MTC derivatives of singly- and doubly-charged TLLELAR. The particular favoring of this fragmentation is attributable to the stronger nucleophilic character of the thiocarbonyl group, in comparison with carbonyl groups available N-terminal to other peptide bonds whose cleavage would give rise to higher members of the b series. Evidently, nucleophilic attack of the thiocarbonyl group is limited to the closest peptide bond, forming a five-membered thiazolone structure.

As further evidence for the proposed mechanism, the CID production spectra for both singly- and doubly-charged ions of the native peptide was compared to the MTC derivative of TLLELAR (again, see FIGS. 22A-22D). Similar to the other arginine-containing peptide, MRFA, the singly-protonated ions, underivatized (FIG. 22A) and MTC-derivatized (see FIG. 22C), show low fragmentation efficiencies due to the localization of the ionizing proton on the side chain of the arginine residue. In the case of the doubly-protonated underivatized peptide (see FIG. 22B), extensive fragmentation was observed. Both qualitative and quantitative features of the spectrum can be readily explained in terms of the predicted locations of the ionizing protons in the [M+2+H]$^{2+}$ precursor ion. The C-terminal arginine residue is expected to sequester a single proton with the second ionizing proton available to promote peptide backbone cleavage via charge-proximal fragmentations. Cleavages of peptide bonds may yield complementary b- and y-series fragments, the stabilities of which will in turn be determined by the extent of localization of the ionizing proton. Thus, for the TLLELAR polypeptide used in this Example, the presence of the C-terminal arginine residue in y-series fragments leads to a strongly localized site of charge with consequent stability to further fragmentation. Accordingly, higher members of the y-series are abundant. In contrast, b series ions incorporate a "mobile" proton and further fragmentation is expected. As a result, only the lower members of the b-series are apparent. In marked contrast, the fragmentation of doubly-protonated derivative (see FIG. 22D) shows selective cleavage of the peptide bond between the first two residues, yielding modified $b_1$ and $y_{n-1}$ ions.

The present invention therefore demonstrates that gas-phase reactions between Edman degradation reagents and protonated peptide ions yields Edman-type derivatives in a fashion directly analogous to the first coupling step in a condensed-phase Edman degradation. The proposed mechanism for the formation of MTC derivative involves proton transfer. Consequently, the coupling reaction with MITC is more efficient for multiply protonated peptides.

The present invention further demonstrates that conversion of peptides to the N-terminal Edman-type derivative introduces a marked propensity for the formation of the derivatized $b_1$, and complementary y ions, to the extent that other fragmentation pathways are not observed under the conditions of low energy collisional activation. The mechanism for formation of modified $b_1$ ion from [M+nH]$^{n+}$ ion of the peptide MITC derivative closely resembles that proposed for peptide fragmentation, in which the "mobile proton" plays a key role.

By combining the two gas phase reactions studied here, gas-phase Edman degradation has been quite readily achieved: protonated peptide ions are first accumulated in an ion trap, where they react with MITC gas to form MTC derivatives. Low energy CID of these peptide MTC derivatives produces exclusively $b_1$ and $y_{n-1}$ ions. The N-terminal amino acid can then be identified by mass determination of $b_1$ ion, and $y_{n-1}$ ion is maintained in the trap for further chemical degradation. Repeating the process reiteratively yields the primary amino acid sequence of the protein or polypeptide being studied, in the same fashion as condensed-phase Edman degradation. As a mass spectrometer can easily detect $10^5$ ions, attomole protein/peptide de novo sequencing is readily achieved by this method.

BIBLIOGRAPHY (1) Edman, P., *Arch. Biochem.* 1949, 22, 475-476.
(2) Edman, P., *Acta Chem. Scand.* 1956, 10, 761-768.
(3) Edman, P. and Begg, G., *Eur J. Biochem.* 1967, 1, 80-91.
(4) Hewick, R. M.; Hunkapiller, M. W.; Hood, L. E.; and Dreyer, W. J., *J. Biol. Chem.* 1981, 256, 7990-7997.
(5) Hempel, J., *Modern Protein Chemistry: Practical Aspects* 2002, 103-122.
(6) Karas, M. and Hillenkamp, F., *Anal. Chem.* 1988, 60, 2299-2301.
(7) Tanaka, K.; Wald, H.; Ido, Y.; Akita, S.; Yoshida, Y.; and Yoshida, T., *Rapid Commun. Mass Spectrom.* 1988, 2, 151-153.
(8) Fenn, I. B.; Mann, M.; Meng, C. K.; Wong, S. F.; and Whitehouse, C. M., *Science* 1989, 246, 64-71.
(9) Puretzky, A. A. and Geohegan, D. B., *Chem. Phys. Len.* 1998, 286, 425-432.
(10) Karas, M.; Gluckmann, M.; Schafer, J., *J. Mass Spectrom.* 2000, 35, 1-12.
(11) Zenobi, R. and Knochenmuss, R., *Mass Spectrom. Rev.* 1998, 17, 337-366.
(12) Ioanoviciu, D., *J. Mass Spectrom. Ion Proc.* 1994, 131, 43-65.
(13) Gui]haus, M., *J. Mass Spectrom.* 1995, 30, 1519-1532.
(14) Vestal, M. and Juhasz, P., *J. Am. Soc. Mass Spectrom.* 1998, 9, 892-911.
(15) Fuerstenau, S. D. and Benner, W. H., *Rapid Commun. Mass Spectrom.* 1995, 9, 1528-1538.
(16) Booth, N. E. and Goldie, D., *J. Supercond. Sci. Technol.* 1996, 9, 493.
(17) Twerenbold, D.; Vuilleumier, J. L.; Gerber, D.; Tadsen, A.; van den Brandt, B.; and Gillevet, P. M., *Appl. Phys. Lett.* 1996, 68, 3503-3505.
(18) Twerenbold, D., *Nucl. Instrum. Methods A* 1996, 370, 253-255.

(19) Twerenbold, D., *Rep. Prog. Phys.* 1996, 59, 349-426.
(20) Frank, M.; Mears, C. A.; Labov, S. E.; Benner, W. H.; Horn, D.; Jakievic, J. M.; and Barfknecht, A. T., *Rapid Commun. Mass Spectrom.* 1996, 10, 1946-1950.
(21) Benner, W. H.; Horn, D. M.; Jaklevic, J. M.; Frank, M.; Mears, C.; Labov, S.; and Barfknecht, A. T., *J. Am. Soc. Mass Spectrorn.* 1997, 8, 1094-1102.
(22) Booth, N. E., *Rapid Commun. Mass Spectrom.* 1997, 11, 944-947.
(23) Westmacott, U.; Frank, M.; Labov, S. E.; and Benner, W. H., *Rapid Commun. Mass Spectrorn.* 2000, 14, 1854-1861.
(24) Westmacott, U.; Zhong, F.; Frank, M.; Friedrich, S.; Labov, S. E.; and Benner, W. H., *Rapid Commun. Mass Spectrorn.* 2000, 14, 600-607.
(25) Miyashita, M.; Presley, J. M.; Buchho]z, B. A.; Lam, K. S.; Lee, Y. M.; Vogel, J. S.; and Hammock, B. D., *Proc. Natl. Acad. Sci.* 2001, 98, 4403-4408.
(26) Biemann, K., *Biomed. Environ. Mass Spectrorn.* 1988, 16, 99-111.
(27) D Agostino, P. A.; Hancock, J. R.; and Provost, L. R. *J. Chrorn. A* 1997, 767, 77-85.
(28) Gevaert, K. and Vandekerckhove, J., *Electrophoresis* 2000, 21, 1145-1154.
(29) Miyashita, M.; Presley, J. M.; Buchholz, B. A.; Lam, K. S.; Lee, Y. M.; Vogel, I. S.; and Hammock, B. D., *Proc. Nati. Acad. Sci.* 2001, 98, 4403-4408.
(30) Chait, B. T.; Wang, R.; Beavis, R. C.; and Kent, S. B. H., *Science* 1993, 262, 89-92.
(31) Summerfield, S. U.; Bolgar, M. S.; and Gaskell, S. J. *J Mass Spectrorn.* 1997, 32, 225-231.
(32) Ebeling, D. D.; Westphall, M. S.; Scaif, M.; and Smith, L. M., *Anal Chem.* 2000, 72, 5158-5161.
(33) Scalf, M.; Westphall, M. S.; Krause, J.; Kaufman, S. L.; and Smith, L. M., *Science* 1999, 283, 194.
(34) Scalf, M.; Westphall. M. S.; and Smith, L. M. *Anal Chem.* 2000, 72. 52-60.
(35) Covey, T. and Douglas, D. I., *J. Am. Soc. Mass Spectrom.* 1993, 4, 616-623.
(36) Javahery, O. and Thomson, B., *J. Am. Soc. Mass Spectrom.* 1997, 8, 697-702.
(37) March, R. E., *J. Mass. Spectrum.* 1997, 32, 351-369.
(38) Campbell, J. M.; Collings. B. A.; and Douglas, D. J., *Rapid Commun. Mass. Spectrum.* 1998, 12, 1463-1474.
(39) Voyksner, R. D. and Lee, Heewon, *Rapid Commun. Mass. Spectrum.* 1999, 13, 1427-1437.
(40) Sannes-Lowery, K.; Griffey, R. H., Kruppa, On; Speir, J. P.; and Hofstadler, S. A., *Rapid Commun. Mass. Spectrum.* 1998, 12, 1957-1961.
(41) Benner, W. H., *Anal Chem.* 1997, 69, 4162-4168.
(42) Drobnica, L. and Augustin, J., *Collection Czechoslov. Chem. Commun.* 1965, 30, 1221-1228.
(43) Lequin, R. M. and Niall, H. D., *Biochim. Biophys. Acta* 1972, 257, 76-82.
(44) van der Rest, O.; He, F.; Emmett, M. R.; Marshall, A. O.; and Gaskeli, S. I., *J. Am. Soc. Mass Spectrom.* 2001, 12, 288-295.
(45) Summerfield, S. O.; Bologar, M. S.; and Gaskell, S.; *J. Mass. Spectrum.* 1997, 32, 225-231.
(46) Summerfield, S. O.; Steen, H.; O'Malley, M.; and Gaskell, S. J., *J. Mass Spectrom.* 1999, 188.95-103.
(47) Harrison, A. O, *Mass Spectroni. Rev.* 1997, 16, 201-217.
(48) Parker, C. E.; Bursey, M. M.; Smith, R. W.; and Gaskell, S. J., *Journal of Chromatography* 1985. 347, 61-74.
(49) Dongre, A. R.; Jones, J. L.; Somogyi, A.; Wysocki, V. H., *J. Am. Chem. Soc.*, 1996, 118, 8365-8374.
(50) Lock, C. M. and Dyer, E., *Rapid Commun. Mass Spectrom.*, 1999, 13, 432-448.
(51) Marzluff, E. M.; Campbell, S.; Rodgers, M. T.; and Beauchamp, J. L., *J. Am. Chem. Soc.* 1994, 116, 6947-6948.
(52) McKeown, P. J. and Johnston, M. V., *J. Am. Soc. Mass Spectrom.*, 1991, 2, 103-107.
(53) Griffin, L. L. and McAdoo, D. J., *J. Am. Soc. Mass Spectrom.*, 1993, 4, 11-15.
(54) Roepstorff, P. and Fohlman, J., *Biomed. Mass Spectrom.* 1984, 11, 601.
(55) Smith, R. D.; Loo, J. A.; Barinaga, C. J.; Edmonds, C. G.; and Udseth, H. R., *J. Am. Soc. Mass. Spectrom,* 1990, 1, 53-65.
(56) Miller, P. E. and Denton, M. B., *J. Chem. Edu.* 1986, 63, 617-622.
(57) Levine, R. D. and Bernstein, R. B., *Molecular Reaction Dynamics and Chemical Reactivity* Oxford University Press: New York, 1987.
(58) Covey, T. and Douglas, D. J., *J. Am. Soc. Mass Spectrom,* 1993, 4, 616-623.
(59) Rao et al., *J. Aerosol Sci.,* 1993, 24, 879-892.
(60) Ziemann et al., *J. Aerosol Sci.* 1995, 26, 745-756.
(61) Liu et al., *Aerosol. Sci. Technol.,* 1995, 22, 293-313.
(62) Liu et al. *Aerosol. Sci. Technol.* 1995, 22, 314-324.
(63) Park et al. *Rapid Commun. Mass Spectrom,* 1994, 8, 317-322.
(64) Imrie et al., *Rapid Commun. Mass Spectrom,* 1995, 9, 1293-1296.
(65) Bahr et al., *Int. J. Mass Spectrom. Ion Proc.,* 1996, 153, 9-21.
(66) Drobnica, L. and Augustin, J., *Collection Czechoslov. Chem. Commun.* 1965, 30, 99-104.

What is claimed is:

1. A method of identifying an amino acid residue of a polypeptide, the method comprising:
   ionizing a polypeptide reactant via matrix-assisted laser desorption/ionization or electrospray ionization; and then
   (a) performing a peptide degradation reaction on the polypeptide ion reactant in the gas phase, wherein the reaction yields a first ion product corresponding to a first amino acid residue of the polypeptide reactant and a polypeptide fragment ion; then
   (b) determining a mass-to-charge ratio for the first ion product, or the polypeptide fragment ion, or both; and then
   (c) identifying the first amino acid residue of the polypeptide reactant from the mass-to-charge ratio determined in step (b).

2. The method of claim 1, further comprising, after step (c):
   repeating steps (a), (b), and (c) to determine part or all of an amino acid sequence of the polypeptide reactant.

3. The method of claim 1, wherein step (a) comprises performing a gas-phase Edman degradation on the polypeptide reactant.

4. The method of claim 1, wherein:
   step (a) comprises performing the peptide degradation reaction on a plurality of different polypeptide reactants simultaneously; wherein the reaction yields a corresponding plurality of first ion products and a corresponding plurality of polypeptide fragment ions;
   step (b) comprises determining the mass-to-charge ratios for the corresponding plurality of polypeptide fragment ions; and
   step (c) comprises identifying the first amino acid residue of each polypeptide reactant from the mass-to-charge ratio determined in step (b).

5. The method of claim 1, wherein the peptide degradation reaction takes place within an ion trap.

6. The method of claim 5, wherein step (a) comprises:
   (i) confining the polypeptide reactant within a linear ion trap; and then
   (ii) contacting the polypeptide reactant with an Edman reagent to yield a thiocarbamoyl-containing intermediate; and then
   (iii) contacting the thiocarbamoyl intermediate with an acid to yield a thiazolinone-containing ion as the first ion product.

7. The method of claim 6, wherein step (ii) comprising contacting the polypeptide reactant with an Edman reagent selected from the group consisting of alkylisothiocyanates, substituted alkylthiocyanates, arylisothiocyanates, and substituted arylisothiocyanates.

8. The method of claim 5, wherein step (a) comprises:
   (i) confining the polypeptide reactant within a linear ion trap; and then
   (ii) contacting the polypeptide reactant with an Edman reagent to yield a thiocarbamoyl intermediate; and then
   (iii) subjecting the thiocarbamoyl intermediate to collision-induced dissociation to yield the first ion product.

9. The method of claim 8, wherein step (ii) comprising contacting the polypeptide reactant with an Edman reagent selected from the group consisting of alkylisothiocyanates, substituted alkylthiocyanates, arylisothiocyanates, and substituted arylisothiocyanates.

10. A method of determining an amino acid sequence of a polypeptide, the method comprising:
    (a) performing a gas-phase peptide degradation reaction on a polypeptide reactant within an ion trap, wherein the reaction yields a first ion product corresponding to a first N-terminal amino acid residue of the polypeptide reactant and a polypeptide fragment ion; then
    (b) selectively transmitting the first ion product from the ion trap into a mass spectrometer and determining a mass-to-charge ratio for the first ion product, wherein the chemical identity of the first amino acid residue of the polypeptide reactant is determined;
    (c) repeating steps (a) and (b) to determine part or all of the amino acid sequence of the polypeptide reactant.

11. The method of claim 10, wherein step (a) comprises:
    (i) confining the polypeptide reactant within a linear ion trap; and then (ii) subjecting the polypeptide reactant to an Edman degradation reaction.

12. The method of claim 10, wherein step (a) comprises:
(i) confining the polypeptide reactant within a linear ion trap; and then
(ii) contacting the polypeptide reactant with an Edman reagent to yield a thiocarbamoyl-containing intermediate; and then
(iii) contacting the thiocarbamoyl intermediate with an acid to yield a thiazolinone-containing ion as the first ion product.

13. The method of claim 12, wherein step (ii) comprising contacting the polypeptide reactant with an Edman reagent selected from the group consisting of alkylisothiocyanates, substituted alkylthiocyanates, arylisothiocyanates, and substituted arylisothiocyanates.

14. The method of claim 10, wherein step (a) comprises:
(i) confining the polypeptide reactant within a linear ion trap; and then
(ii) contacting the polypeptide reactant with an Edman reagent to yield a thiocarbamoyl intermediate; and then
(iii) subjecting the thiocarbamoyl intermediate to collision-induced dissociation to yield the first ion product.

15. The method of claim 10, wherein step (ii) comprising contacting the polypeptide reactant with an Edman reagent selected from the group consisting of alkylisothiocyanates, substituted alkylthiocyanates, arylisothiocyanates, and substituted arylisothiocyanates.

16. The method of claim 10, wherein step (b) comprises selectively transmitting the first ion product into an orthogonal time-of-flight mass spectrometer.

17. The method of claim 10, wherein step (b) comprises selectively transmitting the first ion product into a quadrupole mass analyzer and then transmitting the first ion product into an orthogonal time-of-flight mass spectrometer.

18. A method of determining an amino acid sequence of a polypeptide, the method comprising:
(a) ionizing a polypeptide reactant to yield a polypeptide reactant ion; then
(b) trapping the polypeptide reactant ion within a linear ion trap in the gas phase; then
(c) contacting the polypeptide reactant ion within the linear ion trap and in the gas phase with an Edman reagent to yield a thiocarbamoyl intermediate; then
(d) subjecting the thiocarbamoyl intermediate to collision-induced dissociation, or contacting the thiocarbamoyl intermediate with an acid, to yield a first ion product; and then
(e) selectively transmitting the first ion product from the ion trap into a mass spectrometer and determining a mass-to-charge ratio for the first ion product, wherein a chemical identity for the first N-terminal amino acid residue of the polypeptide reactant is determined.

19. The method of claim 18, wherein step (e) comprises selectively transmitting the first ion product into an orthogonal time-of-flight mass spectrometer.

20. The method of claim 18, wherein step (e) comprises selectively transmitting the first ion product into a quadrupole mass analyzer and then transmitting the first ion product into an orthogonal time-of-flight mass spectrometer.

* * * * *

UNITED STATES PATENT AND TRADEMARK OFFICE
CERTIFICATE OF CORRECTION

PATENT NO. : 8,628,974 B2
APPLICATION NO. : 11/568536
DATED : January 14, 2014
INVENTOR(S) : Xiaoyu Chen et al.

Page 1 of 1

It is certified that error appears in the above-identified patent and that said Letters Patent is hereby corrected as shown below:

In the Specification

Column 1, Lines 17-19:
Delete the phrase:
"This invention was made with United States government support awarded by the following agencies: NIH HV28182. The United States has certain rights in this invention."
And replace with:
--This invention was made with government support under HV028182 awarded by the National Institutes of Health. The government has certain rights in the invention.--.

Signed and Sealed this
Eighth Day of December, 2020

Andrei Iancu
*Director of the United States Patent and Trademark Office*